US007556810B2

(12) United States Patent
Mehta et al.

(10) Patent No.: US 7,556,810 B2
(45) Date of Patent: *Jul. 7, 2009

(54) COMPOSITIONS AND METHODS TO CONTROL ANGIOGENESIS WITH CUPREDOXINS

(75) Inventors: Rajeshwari R. Mehta, Orland Park, IL (US); Brad N. Taylor, Chicago, IL (US); Tohru Yamada, Oak Park, IL (US); Craig W. Beattie, Chicago, IL (US); Tapas K. Das Gupta, River Forest, IL (US); Ananda M. Chakrabarty, Villa Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/488,693

(22) Filed: Jul. 19, 2006

(65) Prior Publication Data

US 2008/0103087 A1 May 1, 2008

Related U.S. Application Data

(60) Provisional application No. 60/700,297, filed on Jul. 19, 2005.

(51) Int. Cl.
*A61K 39/00* (2006.01)
*A61K 39/38* (2006.01)
*A61K 39/02* (2006.01)

(52) U.S. Cl. ............... 424/185.1; 424/9.1; 424/9.2; 424/184.1; 424/190.1; 424/192.1; 424/234.1; 424/250.1; 424/253.1; 424/260.1; 530/300; 530/350; 536/23.1; 536/23.7

(58) Field of Classification Search ............... 424/9.1, 424/9.2, 184.1, 185.1, 190.1, 192.1, 234.1, 424/250.1, 253.1, 260.1; 530/300, 350; 536/23.1, 536/23.7
See application file for complete search history.

(56) References Cited

U.S. PATENT DOCUMENTS

| 7,301,010 | B2 * | 11/2007 | Chakrabarty et al. | 530/350 |
| 7,338,766 | B2 * | 3/2008 | Chakrabarty et al. | 435/6 |
| 2002/0110872 | A1 | 8/2002 | Chakrabarty et al. | |
| 2005/0037341 | A1 | 2/2005 | Dierynck et al. | |

FOREIGN PATENT DOCUMENTS

| WO | WO 02/076380 A3 | 10/2002 |
| WO | WO2004/046177 | 6/2004 |
| WO | 2005/018662 | 3/2005 |
| WO | 2006/088506 | 8/2006 |

OTHER PUBLICATIONS

Sridhar, S.S., et al. Targeting angiogenesis: a review of angiogenesis inhibitors in the treatment of lung cancer. Lung Cancer, vol. 42, pp. S81-S91, 2003.*

Yamada, Tohru et al. Cellular Microbiology, vol. 7, No. 10, 1418-1431 (2005).

Hong CS et al., Cell Cycle, vol. 5 No. 15, 1633-1641 (2006).

Yamada et al., "The Bacterial Redox Protein Azurin Induces Apoptosis in J774 Macrophages through Complex Formation and Stabilization of the Tumor Suppressor Protein p53", *Infection and Immunity*, vol. 70 (12), Dec. 2002, pp. 7054-7062.

Anonymous: "Plastocyanin precursor" DATABASE EMBL, Online, Nov. 1, 1997, XP002306632 abstract.

Anonymous: "Rusticyanin precursor" DATABASE EMBL, Online, Mar. 1, 1992, XP002306633 abstract.

Anonymous: "Pseudoazurin precursor" DATABASE EMBL, Online, Feb. 1, 1991, XP002306634 abstract.

Yamada T, et al., "Internalization of bacterial redox protein azurin in mammalian cells: entry domain and specificity", *Cell Microbiol*. Oct. 2005;7(10):1418-31.

Yamada T, et al., "Rusticyanin, a bacterial electron transfer protein, causes G1 arrest in J774 and apoptosis in human cancer cells", *Cell Cycle* Sep. 2004;3(9):1182-7.

Yamada, T, et al., "Regulation of mammalian cell growth and death by bacterial redox proteins: relevance to ecology and cancer therapy", *Cell Cycle* Jun. 2004;3(6):752-5.

Hiraoka Y, et al., "Modulation of mammalian cell growth and death by prokaryotic and eukaryotic cytochrome c", *Proc Natl Acad Sci U S A*. Apr. 27, 2004;101(17):6427-32.

Yamada T, et al., "Apoptosis or growth arrest: Modulation of tumor suppressor p53's specificity by bacterial redox protein azurin", *Proc Natl Acad Sci U S A*. Apr. 6, 2004;101(4):4770-5.

Punj V, et al., "Bacterial cupredoxin azurin as an inducer of apoptosis and regression in human breast cancer", *Oncogene* Mar. 25, 2004;23(13):2367-78.

Chakrabarty AM, "Microorganisms and Cancer: Quest for a Therapy", *J. Bacteriol*. 185(9):2683-86, 2003.

Punj V, et al., "Bacterial cupredoxin azurin and its interactions with the tumor suppressor protein p53", *Biochem Biophys Res Commun*. Dec. 5, 2003;312(1):109-14.

Punj V, et al., "Energy-generating enzymes of *Burkholderia cepacia* and their interactions with macrophages", *J Bacteriol*. May 2003;185(10):3167-78.

(Continued)

*Primary Examiner*—Rodney P. Swartz
(74) *Attorney, Agent, or Firm*—Sheppard, Mullin, Richter & Hampton LLP

(57) ABSTRACT

The present invention relates to compositions comprising cupredoxins, and their use to inhibit angiogenesis in mammalian cells, tissues, and animals, and particularly the angiogenesis that accompanies tumor development and particularly in humans. Specifically, the present invention relates to compositions comprising the cupredoxin(s), and or peptides that are variants, derivatives or structural equivalents of cupredoxins, which retain the ability to inhibit angiogenesis in mammalian cells, tissues or animals. These compositions may be peptides or pharmaceutical compositions, among others. The compositions of the invention may be used to treat any pathological condition that has as a symptom or cause, inappropriate angiogenesis, and particularly inappropriate angiogenesis related to tumor development.

5 Claims, 8 Drawing Sheets

OTHER PUBLICATIONS

Goto M, et al., "Induction of apoptosis in macrophages by *Pseudomonas aeruginosa* azurin: tumour-suppressor protein p53 and reactive oxygen species, but not redox activity, as critical elements in cytotoxicity", *Mol Microbiol*. Jan. 2003;47(2):549-59.

Yamada T, et al., "The bacterial redox protein azurin induces apoptosis in J774 macrophages through complex formation and stabilization of the tumour suppressor protein p53", *Infect Immun*. Dec. 2002;70(12):7054-62.

Yamada T, et al., "Bacterial redox protein azurin tumor suppressor protein p53, and regression of cancer", *Proc Natl Acad Sci USA*. Oct. 29, 2002;99(22):14098-103. Epub Oct. 22, 2002.

Zaborina O, et al., "P2Z-Independent and P2Z receptor-mediated macrophage killing by *Pseudomonas aeruginosa* isolated from cystic fibrosis patients", *Infect Immun*. Oct. 1999;67(10):5231-42.

Zaborina O, et al., "Secreted products of a nonmucoid *Pseudomonas aeruginosa* strain induce two modes of macrophage killing: external-ATP-dependent, P2Z-receptor-mediated necrosis and ATP-independent, caspase-mediated apoptosis", *Microbiology* Oct. 2000;146 (Pt10):2521-30.

Yang D., et al., "Bacterial redox protein azurin induce apoptosis in human osteosarcoma U2OS cells", *Pharmacological Research* 2005 52(5):413-421.

Apiyo D. and Wittung-Stafshede, P., "Unique complex between bacterial azurin and tumor-suppressor protein p53", *Bioche. Biophys. Res. Comm*. 2005 332: 965-968.

Ye, Z., et al. "Selective inducement effect of bacterial redox protein azurin on apoptosis of human osteosarcoma cell line U2OS", *Chinese Journal of Cancer* 2005, 24(3): 298-304.

Yamada, Tohru et al. Cellular Microbiology, vol. 7, No. 10, 1416-1431 (2005).

Xu R. et al., Database GENESCO (online), "Azurin as a bacterial protein with wide spectrum antitumor function and its use and medical composition", Abstract, Jun. 2004.

Gotschlich & Seiff, FEMS Microbiol. Lett. 43:253-255 (1987).

Kawula, et al., Mol. Microbiol. 1:179-185 (1987).

Hayashi & Wu. J. Bioenerg. Biomembr. 22:451-471 (1990).

Futaki et al., J. Biol. Chem. 276(8):5836-40 (2001).

Papo et al., Cancer Res. 64(16):5779-86 (2004).

Miller et al, Biochem. Pharmacol. 36(1):169-76. (1987).

Lee et al., J. Pept. Res. 63(2):69-84 (2004).

Schafmeister et al., J. Am. Chem. Soc. 122:5891-5892 (2000).

Walenski et al., Science 305:1466-1470 (2004).

* cited by examiner

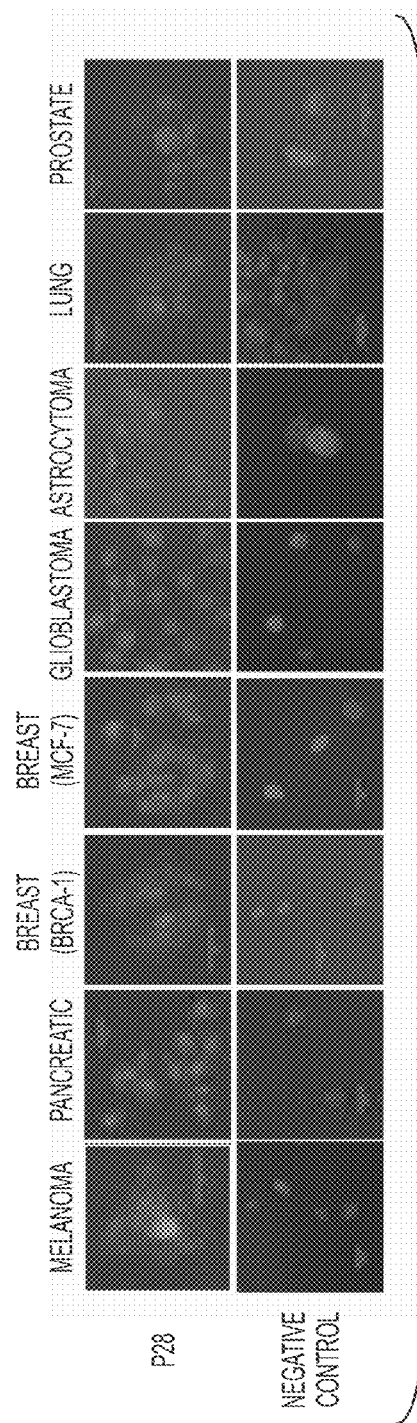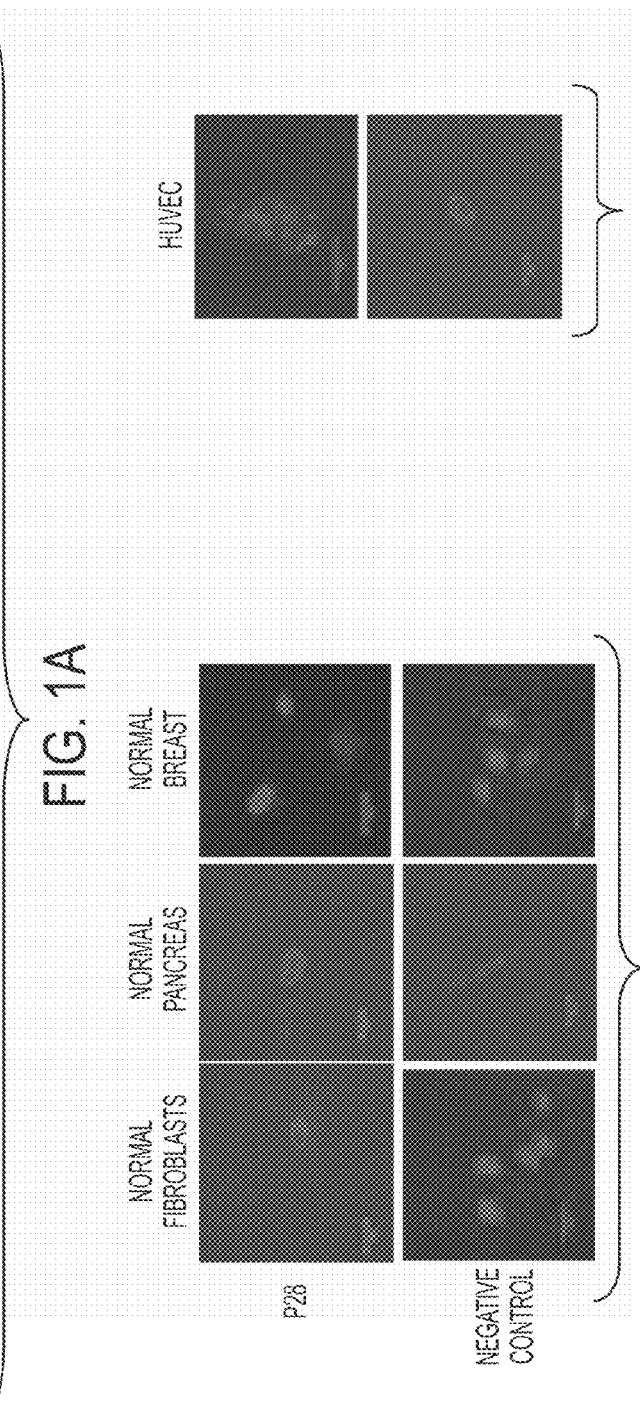

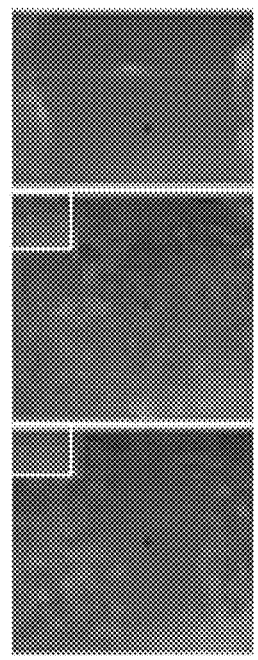
FIG. 3A
FIG. 3B
FIG. 3C
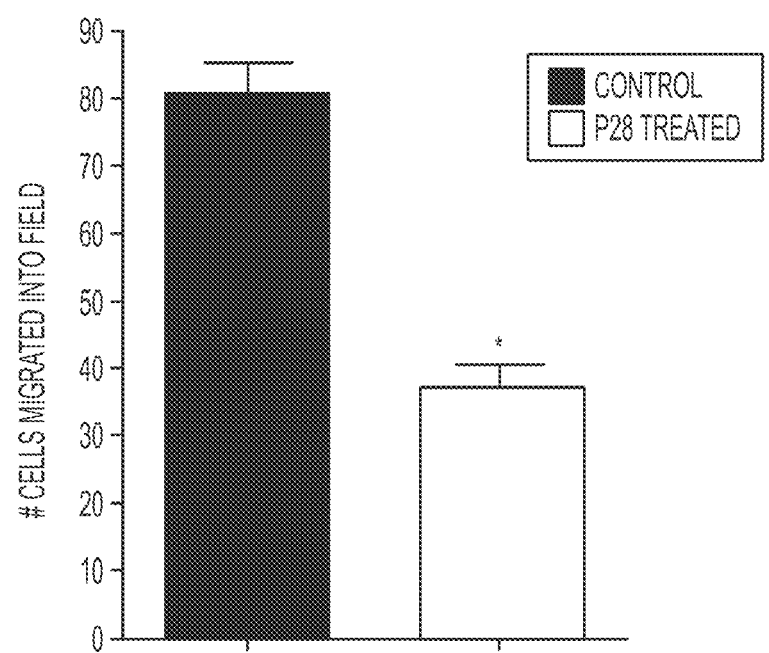
FIG. 3D

SEQUENCE LISTING

<160> NUMBER OF SEQ ID NOS: 25

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn

```
                1               5                      10                      15
Thr Asn Ala Ile Thr Val Asp Lys Ser Cys Lys Gln Phe Thr Val Asn
                        20                      25                      30

Leu Ser His Pro Gly Asn Leu Pro Lys Asn Val Met Gly His Asn Trp
            35                      40                      45

Val Leu Ser Thr Ala Ala Asp Met Gln Gly Val Val Thr Asp Gly Met
        50                      55                      60

Ala Ser Gly Leu Asp Lys Asp Tyr Leu Lys Pro Asp Asp Ser Arg Val
65                      70                      75                      80

Ile Ala His Thr Lys Leu Ile Gly Ser Gly Glu Lys Asp Ser Val Thr
                    85                      90                      95

Phe Asp Val Ser Lys Leu Lys Glu Gly Glu Gln Tyr Met Phe Phe Cys
                100                     105                     110

Thr Phe Pro Gly His Ser Ala Leu Met Lys Gly Thr Leu Thr Leu Lys
                115                     120                     125

<210> SEQ ID NO 2
<211> LENGTH: 28
<212> TYPE: PRT
<213> ORGANISM: Pseudomonas aeruginosa

<400> SEQUENCE: 2

Leu Ser Thr Ala Ala Asp Met Gln Gly Val Val Thr Asp Gly Met Ala
1               5                       10                      15

Ser Gly Leu Asp Lys Asp Tyr Leu Lys Pro Asp Asp
            20                      25

<210> SEQ ID NO 3
<211> LENGTH: 105
<212> TYPE: PRT
<213> ORGANISM: Phormidium laminosum

<400> SEQUENCE: 3

Glu Thr Phe Thr Val Lys Met Gly Ala Asp Ser Gly Leu Leu Gln Phe
1               5                       10                      15

Glu Pro Ala Asn Val Thr Val His Pro Gly Asp Thr Val Lys Trp Val
            20                      25                      30

Asn Asn Lys Leu Pro Pro His Asn Ile Leu Phe Asp Asp Lys Gln Val
        35                      40                      45

Pro Gly Ala Ser Lys Glu Leu Ala Asp Lys Leu Ser His Ser Gln Leu
    50                      55                      60

Met Phe Ser Pro Gly Glu Ser Tyr Glu Ile Thr Phe Ser Ser Asp Phe
65                      70                      75                      80

Pro Ala Gly Thr Tyr Thr Tyr Tyr Cys Ala Pro His Arg Gly Ala Gly
                    85                      90                      95

Met Val Gly Lys Ile Thr Val Glu Gly
                100                     105

<210> SEQ ID NO 4
<211> LENGTH: 155
<212> TYPE: PRT
<213> ORGANISM: Thiobacillus ferrooxidans

<400> SEQUENCE: 4

Gly Thr Leu Asp Thr Thr Trp Lys Glu Ala Thr Leu Pro Gln Val Lys
1               5                       10                      15

Ala Met Leu Glu Lys Asp Thr Gly Lys Val Ser Gly Asp Thr Val Thr
            20                      25                      30
```

```
Tyr Ser Gly Lys Thr Val His Val Ala Ala Val Leu Pro Gly
        35                  40                  45

Phe Pro Phe Pro Ser Phe Glu Val His Asp Lys Lys Asn Pro Thr Leu
 50                  55                  60

Glu Ile Pro Ala Gly Ala Thr Val Asp Val Thr Phe Ile Asn Thr Asn
 65                  70                  75                  80

Lys Gly Phe Gly His Ser Phe Asp Ile Thr Lys Gly Pro Pro Tyr
                 85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
                115                 120                 125

Pro Thr Ala Gly Thr Tyr Tyr Tyr Val Cys Gln Ile Pro Gly His Ala
                130                 135                 140

Ala Thr Gly Met Phe Gly Lys Ile Val Val Lys
145                 150                 155

<210> SEQ ID NO 5
<211> LENGTH: 124
<212> TYPE: PRT
<213> ORGANISM: Achromabacter cycloclastes

<400> SEQUENCE: 5

Ala Asp Phe Glu Val His Met Leu Asn Lys Gly Lys Asp Gly Ala Met
 1               5                  10                  15

Val Phe Glu Pro Ala Ser Leu Lys Val Ala Pro Gly Asp Thr Val Thr
                 20                  25                  30

Phe Ile Pro Thr Asp Lys Gly His Asn Val Glu Thr Ile Lys Gly Met
                 35                  40                  45

Ile Pro Asp Gly Ala Glu Ala Phe Lys Ser Lys Ile Asn Glu Asn Tyr
                 50                  55                  60

Lys Val Thr Phe Thr Ala Pro Gly Val Tyr Gly Val Lys Cys Thr Pro
 65                  70                  75                  80

His Tyr Gly Met Gly Met Val Gly Val Val Gln Val Gly Asp Ala Pro
                 85                  90                  95

Ala Asn Leu Glu Ala Val Lys Gly Ala Lys Asn Pro Lys Lys Ala Gln
                100                 105                 110

Glu Arg Leu Asp Ala Ala Leu Ala Ala Leu Gly Asn
                115                 120

<210> SEQ ID NO 6
<211> LENGTH: 128
<212> TYPE: PRT
<213> ORGANISM: Alcaligenes faecalis

<400> SEQUENCE: 6

Ala Cys Asp Val Ser Ile Glu Gly Asn Asp Ser Met Gln Phe Asn Thr
 1               5                  10                  15

Lys Ser Ile Val Val Asp Lys Thr Cys Lys Glu Phe Thr Ile Asn Leu
                 20                  25                  30

Lys His Thr Gly Lys Leu Pro Lys Ala Ala Met Gly His Asn Val Val
                 35                  40                  45

Val Ser Lys Lys Ser Asp Glu Ser Ala Val Ala Thr Asp Gly Met Lys
                 50                  55                  60

Ala Gly Leu Asn Asn Asp Tyr Val Lys Ala Gly Asp Glu Arg Val Ile
 65                  70                  75                  80
```

```
Ala His Thr Ser Val Ile Gly Gly Glu Thr Asp Ser Val Thr Phe
                85                  90                  95

Asp Val Ser Lys Leu Lys Glu Gly Glu Asp Tyr Ala Phe Phe Cys Ser
                100                 105                 110

Phe Pro Gly His Trp Ser Ile Met Lys Gly Thr Ile Glu Leu Gly Ser
                115                 120                 125
```

<210> SEQ ID NO 7
<211> LENGTH: 129
<212> TYPE: PRT
<213> ORGANISM: Achromobacter xylosoxidans ssp. denitrificans I

<400> SEQUENCE: 7

```
Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
                20                  25                  30

Leu Lys His Val Gly Lys Met Ala Lys Val Ala Met Gly His Asn Trp
                35                  40                  45

Val Leu Thr Lys Glu Ala Asp Lys Gln Gly Val Ala Thr Asp Gly Met
    50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Glu Ser Asp Ser Val Thr
                85                  90                  95

Phe Asp Val Ser Lys Leu Thr Pro Gly Glu Ala Tyr Ala Tyr Phe Cys
                100                 105                 110

Ser Phe Pro Gly His Trp Ala Met Met Lys Gly Thr Leu Lys Leu Ser
                115                 120                 125

Asn
```

<210> SEQ ID NO 8
<211> LENGTH: 129
<212> TYPE: PRT
<213> ORGANISM: Bordetella bronchiseptica

<400> SEQUENCE: 8

```
Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
                20                  25                  30

Leu Lys His Thr Gly Lys Leu Pro Arg Asn Val Met Gly His Asn Trp
                35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
                85                  90                  95

Phe Asp Val Ala Lys Leu Ala Ala Gly Asp Asp Tyr Thr Phe Phe Cys
                100                 105                 110

Ser Phe Pro Gly His Gly Ala Leu Met Lys Gly Thr Leu Lys Leu Val
                115                 120                 125

Asp
```

```
<210> SEQ ID NO 9
<211> LENGTH: 129
<212> TYPE: PRT
<213> ORGANISM: Methylomonas sp. J.

<400> SEQUENCE: 9
```

Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
        35                  40                  45

Val Leu Ala Lys Ser Ala Asp Val Gly Asp Val Ala Lys Glu Gly Ala
    50                  55                  60

His Ala Gly Ala Asp Asn Asn Phe Val Thr Pro Gly Asp Lys Arg Val
65                  70                  75                  80

Ile Ala Phe Thr Pro Ile Ile Gly Gly Gly Glu Lys Thr Ser Val Lys
                85                  90                  95

Phe Lys Val Ser Ala Leu Ser Lys Asp Glu Ala Tyr Thr Tyr Phe Cys
            100                 105                 110

Ser Tyr Pro Gly His Phe Ser Met Met Arg Gly Thr Leu Lys Leu Glu
        115                 120                 125

Glu

```
<210> SEQ ID NO 10
<211> LENGTH: 166
<212> TYPE: PRT
<213> ORGANISM: Neisseria meningitidis

<400> SEQUENCE: 10
```

Cys Ser Gln Glu Pro Ala Ala Pro Ala Ala Glu Ala Thr Pro Ala Ala
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala Gly Asn Cys Ala Ala Thr Val Glu Ser
        35                  40                  45

Asn Asp Asn Met Gln Phe Asn Thr Lys Asp Ile Gln Val Ser Lys Ala
    50                  55                  60

Cys Lys Glu Phe Thr Ile Thr Leu Lys His Thr Gly Thr Gln Pro Lys
65                  70                  75                  80

Thr Ser Met Gly His Asn Ile Val Ile Gly Lys Thr Glu Asp Met Asp
                85                  90                  95

Gly Ile Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Glu
    130                 135                 140

Tyr Lys Phe Ala Cys Thr Phe Pro Gly His Gly Ala Leu Met Asn Gly
145                 150                 155                 160

Lys Val Thr Leu Val Asp
                165

```
<210> SEQ ID NO 11
<211> LENGTH: 128
<212> TYPE: PRT
<213> ORGANISM: Pseudomomas fluorescens
```

<400> SEQUENCE: 11

```
Ala Glu Cys Lys Thr Thr Ile Asp Ser Thr Asp Gln Met Ser Phe Asn
1               5                   10                  15

Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
    50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125
```

<210> SEQ ID NO 12
<211> LENGTH: 128
<212> TYPE: PRT
<213> ORGANISM: Pseudomonas chlororaphis

<400> SEQUENCE: 12

```
Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
    50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125
```

<210> SEQ ID NO 13
<211> LENGTH: 129
<212> TYPE: PRT
<213> ORGANISM: Xylella fastidiosa 9a5c

<400> SEQUENCE: 13

```
Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
    50                  55                  60
```

-continued

His Ala Thr Leu Ala Asp Asn Tyr Val Pro Lys Ala Asp Pro Arg Val
 65                  70                  75                  80

Ile Ala His Thr Ala Ile Ile Gly Gly Gly Glu Arg Thr Ser Ile Thr
                 85                  90                  95

Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
 1               5                  10                  15

Pro Ser Ser Pro Asn Phe Tyr Ser Gln Trp Ala Ala Gly Lys Thr Phe
             20                  25                  30

Arg Val Gly Asp Ser Leu Gln Phe Asn Phe Pro Ala Asn Ala His Asn
         35                  40                  45

Val His Glu Met Glu Thr Lys Gln Ser Phe Asp Ala Cys Asn Phe Val
     50                  55                  60

Asn Ser Asp Asn Asp Val Glu Arg Thr Ser Pro Val Ile Glu Arg Leu
 65                  70                  75                  80

Asp Glu Leu Gly Met His Tyr Phe Val Cys Thr Val Gly Thr His Cys
                 85                  90                  95

Ser Asn Gly Gln Lys Leu Ser Ile Asn Val Val Ala Ala Asn Ala Thr
            100                 105                 110

Val Ser Met Pro Pro Ser Ser Pro Pro Ser Ser Val Met Pro
        115                 120                 125

Pro Pro Val Met Pro Pro Ser Pro Ser
    130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Met Val Leu Ala Val Leu Thr Ala Met
 1               5                  10                  15

Ala Met Val Leu Ala Ala Cys Gly Gly Gly Ser Ser Gly Gly Ser
             20                  25                  30

Thr Gly Gly Gly Ser Gly Ser Gly Pro Val Thr Ile Glu Ile Gly Ser
         35                  40                  45

Lys Gly Glu Glu Leu Ala Phe Asp Lys Thr Glu Leu Thr Val Ser Ala
     50                  55                  60

Gly Gln Thr Val Thr Ile Arg Phe Lys Asn Asn Ser Ala Val Gln Gln
 65                  70                  75                  80

His Asn Trp Ile Leu Val Lys Gly Gly Glu Ala Glu Ala Ala Asn Ile
                 85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu

```
                    115                 120                 125
Thr Val Glu Val Thr Phe Thr Ala Pro Ala Ala Gly Thr Tyr Leu Tyr
    130                 135                 140

Ile Cys Thr Val Pro Gly His Tyr Pro Leu Met Gln Gly Lys Leu Val
145                 150                 155                 160

Val Asn

<210> SEQ ID NO 16
<211> LENGTH: 140
<212> TYPE: PRT
<213> ORGANISM: Chloroflexus aurantiacus

<400> SEQUENCE: 16

Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Val Ala Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
                100                 105                 110

Pro Ala Pro Gly Thr Tyr Leu Tyr Ile Cys Thr Phe Pro Gly His Tyr
            115                 120                 125

Leu Ala Gly Met Lys Gly Thr Leu Thr Val Thr Pro
        130                 135                 140

<210> SEQ ID NO 17
<211> LENGTH: 96
<212> TYPE: PRT
<213> ORGANISM: Cucumis sativus

<400> SEQUENCE: 17

Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Asn Gln Gly Gly
        35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95

<210> SEQ ID NO 18
<211> LENGTH: 166
<212> TYPE: PRT
<213> ORGANISM: Neisseria gonorrhoeae F62

<400> SEQUENCE: 18
```

```
Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
                20                  25                  30

Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
        50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Asp
130                 135                 140

Tyr Lys Phe Ala Cys Thr Phe Pro Gly His Gly Ala Leu Met Asn Gly
145                 150                 155                 160

Lys Val Thr Leu Val Asp
                165
```

<210> SEQ ID NO 19
<211> LENGTH: 150
<212> TYPE: PRT
<213> ORGANISM: Vibrio parahaemolyticus

<400> SEQUENCE: 19

```
Met Ser Leu Arg Ile Leu Ala Ala Thr Leu Ala Leu Ala Gly Leu Ser
1               5                   10                  15

Phe Gly Ala Gln Ala Ser Ala Glu Cys Glu Val Ser Ile Asp Ala Asn
                20                  25                  30

Asp Met Met Gln Phe Ser Thr Lys Thr Leu Ser Val Pro Ala Thr Cys
            35                  40                  45

Lys Glu Val Thr Leu Thr Leu Asn His Thr Gly Lys Met Pro Ala Gln
        50                  55                  60

Ser Met Gly His Asn Val Val Ile Ala Asp Thr Ala Asn Ile Gln Ala
65                  70                  75                  80

Val Gly Thr Asp Gly Met Ser Ala Gly Ala Asp Asn Ser Tyr Val Lys
                85                  90                  95

Pro Asp Asp Glu Arg Val Tyr Ala His Thr Lys Val Gly Gly Gly
            100                 105                 110

Glu Ser Thr Ser Ile Thr Phe Ser Thr Glu Lys Met Thr Ala Gly Gly
        115                 120                 125

Asp Tyr Ser Phe Phe Cys Ser Phe Pro Gly His Trp Ala Ile Met Gln
130                 135                 140

Gly Lys Phe Glu Phe Lys
145                 150
```

<210> SEQ ID NO 20
<211> LENGTH: 33
<212> TYPE: PRT
<213> ORGANISM: Chloroflexus aurantiacus

<400> SEQUENCE: 20

```
His Asn Trp Val Leu Asn Gly Gly Asp Asp Val Ala Ala Val
1               5                  10                 15

Asn Thr Ala Ala Gln Asn Asn Ala Asp Ala Leu Phe Val Pro Pro
            20              25                  30

Asp
```

<210> SEQ ID NO 21
<211> LENGTH: 28
<212> TYPE: PRT
<213> ORGANISM: Bordetella pertussis

<400> SEQUENCE: 21

```
Leu Thr Lys Thr Ala Asp Met Gln Ala Val Glu Lys Asp Gly Ile Ala
1               5                   10                  15

Ala Gly Leu Asp Asn Gln Tyr Leu Lys Ala Gly Asp
            20                  25
```

<210> SEQ ID NO 22
<211> LENGTH: 27
<212> TYPE: PRT
<213> ORGANISM: Neisseria meningitidis

<400> SEQUENCE: 22

```
Ile Gly Lys Thr Glu Asp Met Asp Gly Ile Phe Lys Asp Gly Val Gly
1               5                   10                  15

Ala Ala Asp Thr Asp Tyr Val Lys Pro Asp Asp
            20                  25
```

<210> SEQ ID NO 23
<211> LENGTH: 27
<212> TYPE: PRT
<213> ORGANISM: Pseudomonas syringae

<400> SEQUENCE: 23

```
Ser Lys Lys Ala Asp Ala Ser Ala Ile Thr Thr Asp Gly Met Ser Val
1               5                   10                  15

Gly Ile Asp Lys Asp Tyr Val Lys Pro Asp Asp
            20                  25
```

<210> SEQ ID NO 24
<211> LENGTH: 27
<212> TYPE: PRT
<213> ORGANISM: Vibrio parahaemolyticus

<400> SEQUENCE: 24

```
Ala Asp Thr Ala Asn Ile Gln Ala Val Gly Thr Asp Gly Met Ser Ala
1               5                   10                  15

Gly Ala Asp Asn Ser Tyr Val Lys Pro Asp Asp
            20                  25
```

<210> SEQ ID NO 25
<211> LENGTH: 27
<212> TYPE: PRT
<213> ORGANISM: Bordetella pertussis

<400> SEQUENCE: 25

```
Thr Lys Thr Ala Asp Met Gln Ala Val Glu Lys Asp Gly Ile Ala Ala
1               5                   10                  15

Gly Leu Asp Asn Gln Tyr Leu Lys Ala Gly Asp
            20                  25
```

COMPOSITIONS AND METHODS TO CONTROL ANGIOGENESIS WITH CUPREDOXINS

RELATED APPLICATIONS

This application claims priority under 35 U.S.C. §§ 119 and 120 to U.S. provisional Patent Application 60/700,297, filed Jul. 19, 2005, and U.S. patent application Ser. No. 11/436,592 filed May 19, 2006, which claims priority to U.S. Provisional Patent Application 60/764,749, filed Feb. 3, 2006; and U.S. patent application Ser. No. 11/244,105, filed Oct. 6, 2005, which claims priority to U.S. Provisional Patent Application Ser. No. 60/616,782, filed Oct. 7, 2004, and U.S. Provisional Patent Application Ser. No. 60/680,500, filed May 13, 2005, and is a continuation-in-part of U.S. patent application Ser. No. 10/720,603, filed Nov. 11, 2003, which claims priority to U.S. Provisional Patent Application Ser. No. 60/414,550, filed Aug. 15, 2003, and which is a continuation-in-part of U.S. patent application Ser. No. 10/047,710, filed Jan. 15, 2002, which claims priority to U.S. Provisional Patent Application Ser. No. 60/269,133, filed Feb. 15, 2001. The entire content of these prior applications is fully incorporated herein by reference.

STATEMENT OF GOVERNMENTAL INTEREST

The subject matter of this application has been supported by research grants from the National Institutes of Health (NIH), Bethesda, Md., U.S.A., (Grant Numbers AI 16790-21, ES 04050-16, AI 45541, CA09432 and N01-CM97567). The government may have certain rights in this invention.

FIELD OF THE INVENTION

The present invention relates to cupredoxins and variants, derivatives and structural equivalents of cupredoxins, specifically *Pseudomonas aeruginosa* azurin, and their use in inhibiting angiogenesis in mammals, to treat conditions related to inappropriate angiogenesis in mammals, and in particular in inhibiting angiogenesis associated with tumor development. The invention also relates to pharmaceutical compositions comprising cupredoxins and variants, derivatives and structural equivalents of cupredoxins that can be administered to a mammalian patient, and specifically administered to inhibit angiogenesis.

BACKGROUND

Angiogenesis is the formation of new blood vessels from preexisting endothelial vasculature. Folkman, et al., J. Exp. Med. 133:275-288, (1971). Most tumors require angiogenesis to sustain growth beyond a critical volume of 1-2 mm, when the supply of nutrients and metabolites becomes insufficient due to the limits of diffusional exchange. Folkman, J. Nat. Cancer Inst. 82:4-6 (1990). Tumors deprived of angiogenesis remain dormant indefinitely, only to rapidly grow when a blood supply is acquired. Brem et al., Cancer Res. 36:2807-2812 (1976). The degree of angiogenesis often increases with tumor progression. Dome et al., J. Pathol. 197:355-362 (2002). Further, invasion and metastatic spread of tumors are also thought to be angiogenesis-dependant events. Folkman, Ann Surg. 175:409-416 (1972). The newly formed blood vessels provide a route for cancer cells to enter the circulatory system and spread to distant parts of the body. Fidler and Ellis, Cell 79:185-188 (1994).

Because angiogenesis is an integral process in the growth and spread of tumors, it is an important focus of cancer therapy. Anti-angiogenesis therapy is effective not only for solid tumors, but also hematopoietic tumors, leukemia and myeloma, Bellamy et al., Cancer Res. 59:728-733 (1999); Rajkumar et al., Leukemia. 13:469-472 (1999). Endothelial cells are thought to be better targets for therapy than tumor cells because they have a longer generation time and more genetic stability that tumor cells. Endothelial cells are therefore less likely to "escape" therapy by developing drug resistance to the therapy administered. Boehn-Vaiswanathan, Curr. Opin. Oncol. 12:89-94 (2000).

Other conditions suffered by mammals are also related to inappropriate angiogenesis. Wet macular degeneration occurs when blood capillaries inappropriately grow into the retina. Inappropriate angiogenesis has also been implicated as a fundamental characteristic of diabetic retinopathy, psoriasis and rheumatoid arthritis, among other diseases. Bussolino et al., Trends Biochem. Sci. 22:251-256 (1997); Folkman, Nat. Med. 1: 27-31 (1995).

What is needed are additional therapies for inappropriate angiogenesis, particularly that which occurs during tumor formation. Such therapies may be useful in many conditions that exhibit inappropriate or unwanted formation of new blood vessels.

SUMMARY OF THE INVENTION

The present invention relates to compositions comprising cupredoxins, and their use to inhibit angiogenesis in mammalian cells, tissues, and animals, and particularly the angiogenesis that accompanies tumor development and particularly in humans. Specifically, the present invention relates to compositions comprising the cupredoxin(s), and or peptides that are variants, derivatives or structural equivalents of cupredoxins, which retain the ability to inhibit angiogenesis in mammalian cells, tissues or animals. These compositions may be peptides or pharmaceutical compositions, among others. The compositions of the invention may be used to treat any pathological condition that has as a symptom or cause, inappropriate angiogenesis, and particularly inappropriate angiogenesis related to tumor development.

One aspect of the invention is an isolated peptide that is a variant, derivative or structural equivalent of a cupredoxin and that can inhibit angiogenesis in mammalian cells. The cupredoxin may be azurin, pseudoazurin, plastocyanin, rusticyanin, Laz and auracyanin, and specifically azurin. The cupredoxin may be from *Pseudomonas aeruginosa*, *Alcaligenes faecalis*, *Achromobacter xylosoxidan*, *Bordetella bronchiseptica*, *Methylomonas* sp., *Neisseria meningitidis*, *Neisseria gonorrhea*, *Pseudomonas fluorescens*, *Pseudomonas chlororaphis*, *Xylella fastidiosa* and *Vibrio parahaemolyticus*, and specifically *Pseudomonas aeruginosa*. The isolated peptide may be part of a SEQ ID NOS: 1, 3-19, or be a sequence to which SEQ ID NOS: 1, 3-19 has at least 80% amino acid sequence identity.

The isolated peptide may be a truncation of cupredoxin. In these cases, the isolated peptide may be more than about 10 residues and not more than about 100 residues. The isolated peptide comprises *Pseudomonas aeruginosa* azurin residues 50-77, residues 50-67 or residues 36-88 or SEQ ID NOS: 20-24. Further, the isolated peptide may consist of *Pseudomonas aeruginosa* residues 50-77, residues 50-67 or residues 36-88 or SEQ ID NOS: 20-24. Finally, the isolated peptide may comprise equivalent residues *Pseudomonas aeruginosa* azurin residues 50-77, residues 50-67 or residues 36-88.

Another aspect of the invention is a pharmaceutical composition which comprises at least one cupredoxin or isolated peptide in a pharmaceutically acceptable carrier. This pharmaceutical composition may comprise at least two of the cupredoxins or isolated peptides. Further, the pharmaceutical composition may be formulated for intravenous administration. In some embodiments, the cupredoxin is from *Pseudomonas aeruginosa, Alcaligenes faecalis, Achromobtacter xylosoxidan, Bordetella bronchiseptica, Methylomonas* sp., *Neisseria meningitidis, Neisseria gonorrhea, Pseudomonas fluorescens, Pseudomonas chlororaphis, Xylella fastidiosa* or *Vibrio parahaemolyticus*, and specifically from *Pseudomonas aeruginosa*. The cupredoxin may be SEQ ID NOS: 1, 3-19.

Another aspect of the invention are methods to treat a mammalian patient suffering from a condition related to inappropriate angiogenesis which comprises administering to the patient a therapeutically effective amount of the pharmaceutical composition. In some embodiment the patient is human. The patient may be suffering from cancer, and in particular melanoma, breast, pancreas, glioblastoma, astrocytoma, or lung cancer. In other embodiments, the patient may be suffering from a condition selected from the group consisting of macular degeneration, diabetic retinopathy, psoriasis or rheumatoid arthritis. In these methods, the pharmaceutical composition is administered by intravenous injection, intramuscular injection, subcutaneous injection, inhalation, topical administration, transdermal patch, suppository, vitreous injection or oral, and specifically by intravenous injection.

In some embodiments of the methods, the pharmaceutical composition is co-administered with at least one other anti-cancer drug, and specifically at about the same time as another anti-cancer drug. In other embodiments of the method, the pharmaceutical composition is co-administered with an anti-macular degeneration drug, an anti-diabetic retinopathy drug, an anti-psoriasis drug or an anti-rheumatoid arthritis drug.

Another aspect of the invention is a kit comprising the pharmaceutical composition in a vial. This kit may be designed for intravenous administration.

Another aspect of the invention is a method to study angiogenesis or a condition related to inappropriate angiogenesis, comprising contacting the mammalian cells capable of angiogenesis with a cupredoxin or variant, derivative or structural equivalent of a cupredoxin and measuring the extend of angiogenesis. In some embodiments, the cells are human cells. In other embodiments, the mammalian cells are Human Umbilical Vascular Endothelium Cells (HUVECs).

Another aspect of the invention is an expression vector which encodes a variant, derivative or structural equivalent of a cupredoxin.

These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa*.

SEQ ID NO: 2. Amino acid sequence of P28, *Pseudomonas aeruginosa* azurin residues 50-77.

SEQ ID NO: 3. Amino acid sequence of plastocyanin from *Phormidium laminosum*.

SEQ ID NO: 4. Amino acid sequence of rusticyanin from *Thiobacillus ferrooxidans*.

SEQ ID NO: 5. Amino acid sequence of pseudoazurin from *Achromobacter cycloclastes*.

SEQ ID NO: 6. Amino acid sequence of from *Alcaligenes faecalis*.

SEQ ID NO: 7. Amino acid sequence of azurin from *Achromobacter xylosoxidans* ssp. *denitrificans* I.

SEQ ID NO: 8. Amino acid sequence of azurin from *Bordetella bronchiseptica*.

SEQ ID NO: 9. Amino acid sequence of azurin from *Methylomonas* sp. J.

SEQ ID NO: 10. Amino acid sequence of azurin from *Neisseria meningitidis* Z2491.

SEQ ID NO: 11. Amino acid sequence of azurin from *Pseudomonas fluorescen*.

SEQ ID NO: 12. Amino acid sequence of azurin from *Pseudomonas chlororaphis*.

SEQ ID NO: 13. Amino acid sequence of azurin from *Xylella fastidiosa* 9a5c.

SEQ ID NO: 14. Amino acid sequence of stellacyanin from *Cucumis sativus*.

SEQ ID NO: 15. Amino acid sequence of auracyanin A from *Chloroflexus aurantiacus*.

SEQ ID NO: 16. Amino acid sequence of auracyanin B from *Chloroflexus aurantiacus*.

SEQ ID NO: 17. Amino acid sequence of cucumber basic protein from *Cucumis sativus*.

SEQ ID NO: 18. Amino acid sequence of Laz from *Neisseria gonorrhoeae* F62.

SEQ ID NO: 19. Amino acid sequence of the azurin from *Vibrio parahaemolyticus*.

SEQ ID NO: 20. Amino acid sequence of amino acids 57 to 89 of auracyanin B of *Chloroflexus aurantiacus*.

SEQ ID NO: 21. Amino acid sequence of amino acids 51-77 of *Pseudomonas syringae* azurin.

SEQ ID NO: 22. Amino acid sequence of amino acids 89-115 of *Neisseria meningitidis* Laz.

SEQ ID NO: 23. Amino acid sequence of amino acids 52-78 of *Vibrio parahaemolyticus* azurin.

SEQ ID NO: 24. Amino acid sequence of amino acids 51-77 of *Bordetella bronchiseptica* azurin.

BRIEF DESCRIPTION OF THE FIGURES

FIG. 1. FIG. 1 depicts confocal microscopy images of malignant and normal cells incubated with P28 labeled with Alexafluor® 568 and the cells are then stained with DAPI. The indicated cell lines were incubated in the absence (negative control) or presence (P28) of 20 μM Alexafluor® 568 labeled P28 for 2 h at 37° C. The images are indicative of amount of cellular entry observed. FIG. 1A depicts the Alexafluor® 568 fluorescence and control fluorescence of human melanoma, pancreatic, breast (BCA-1), breast (MCF-7), glioblastoma, astrocytoma, lung and prostrate cancer cells. FIG. 1B depicts the Alexafluor® 568 fluorescence and control fluorescence of human normal fibroblast, pancreas and breast cells. FIG. 1C depicts the Alexafluor® 568 fluorescence and control fluorescence of human umbilical vein endothelial cells (HUVEC).

FIG. 2. FIG. 2 depicts the capillary tube formation by HUVEC cells plated on Matrigel® in the presence or absence of P28. Culture media contained 20 ng/ml VEGF.

FIG. 3. FIG. 3 depicts the results of the scratch wound HUVEC migration assay. In FIGS. 3A-C show the fixed cells that were stained for F-actin and nuclei. In FIG. 3A, HUVEC cells at 90% confluence were scratched using a 1 ml plastic pipette tip. In FIG. 3B, the HUVEC cells were scratched and then incubated in the culture media containing 20 ng/ml VEGF for 24 h at 37° C. in the absence of P28. In FIG. 3C, the HUVEC cells were scratched and then incubated for 24 h at 37° C. in the presence of 25 µM P28. The insets of FIGS. 3A-C show the cell density in the area away from the scored area. In FIG. 3D, a bar graph indicates the average # of cells in 20 different fields (20×) of the scratched area in control and P28 treated wells (FIGS. 3B and C). Data represent mean±SEM. * indicates the differences are statistically significant.

FIG. 4. FIG. 4 depicts the images of the localization of cell structural proteins with and without P28 treatment. HUVEC cells were plated on Matrigel®-coated cover slips, incubated in the culture media containing 20 ng/ml VEGF in the presence or absence of P28 peptide (25 µM) for 4 and 24 h, fixed, and processed for staining of CD31/PECAM-1, paxillin, Fak (focal adhesion kinase), vinculin, WASP (Wiskott Aldrich Syndrome protein) and β-catenin. Each figure pertains to the detection of particular structural protein.

FIG. 5 depicts Mel-2 cells which were treated with increasing concentrations of P28 for 24, 48, and 72 hours. The number of cells in treated and control wells were counted using a Coulter counter. Data represent percentage of cell growth inhibition when compared to control cultures at the time point.

FIG. 6. Depicts the results when Mel-2 cells were injected subcutaneously in the left flank (about 1 million cells/animal). Animals received P28 at the indicated dose at the time of injection.

DETAILED DESCRIPTION OF THE INVENTION

Definitions

Figure 2A:
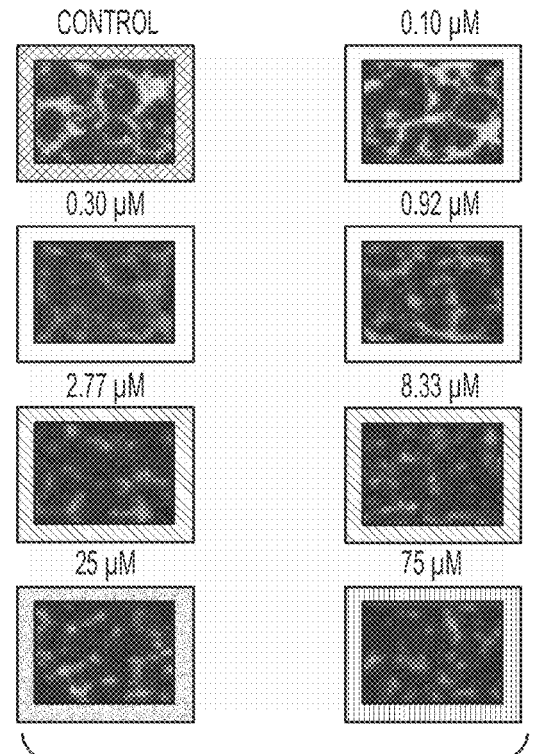
FIG. 2A shows images of HUVEC cells incubated for 4 h at 37° C. with 0.10 μM, 0.30 μM, 0.92 μM, 2.77 μM, 8.33 μM, 25 μM and 75 μM of P28, and then stained with calcein AM and visualized using fluorescence microscopy.
Figure 2B:
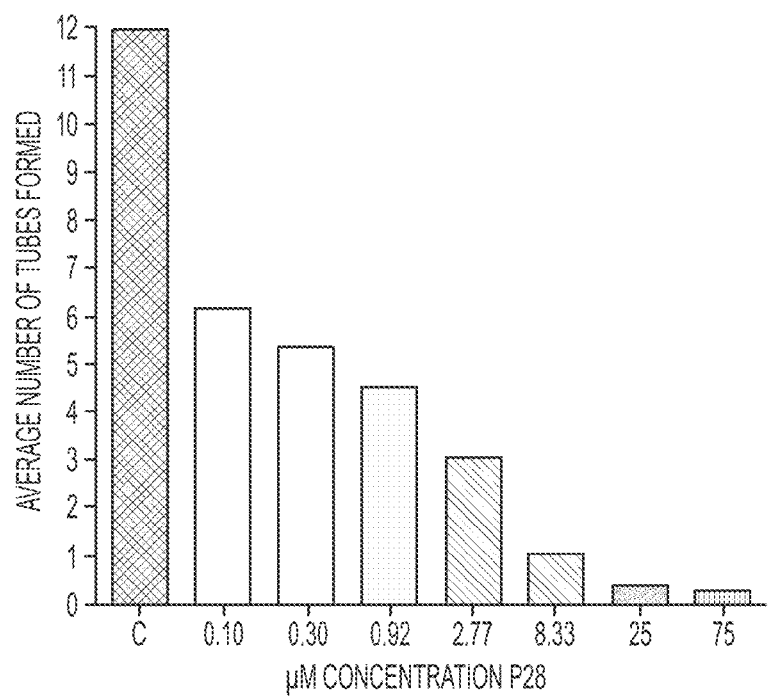
In FIG. 2B, the graph shows the average number of tubes formed in peptide treated and control (untreated) cells.

As used herein, the term "cell" includes either the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate.

As used herein, the term "inhibit cell growth" means the slowing or ceasing of cell division and/or cell expansion. This term also includes the inhibition of cell development or increases in cell death.

As used herein, the term "inhibit angiogenesis" refers to the slowing, ceasing or reverse of the formation of blood vessels in a particular cells, tissues, or location of the body. The inhibition of angiogenesis may be due to direct or indirect effects on endothelial cells. The inhibition may also be at any stage of the angiogenesis process. For example, the inhibition may be due to preventing a tumor from producing Vascular Endothelial Growth Factor (VEGF), direct inhibition of endothelial cell proliferation and/or migration, acting as an antagonist of angiogenesis growth factors, inhibition of endothelial-specific integrin/survival signaling, or chelation of copper. The inhibition of angiogenesis may be by any means by which the formation of blood vessels is slowed, ceased or reversed, including any means currently used by any anti-angiogenesis drug under development or on the market.

As used herein, the term "inappropriate angiogenesis" refers to any occurrence of angiogenesis that is undesirable. Inappropriate angiogenesis may be angiogenesis that is associated with a condition in a mammal. The inappropriate angiogenesis may be either the cause or the symptom of such a condition. Inappropriate angiogenesis in a broader sense may be any angiogenesis that is unwanted, even though it may be within the realm of normal mammalian physiology.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure," as used herein, when used to modify a protein or other cellular product of the invention, refers to, for example, a protein isolated from the growth medium or cellular contents, in a form substantially free of, or unadulterated by, other proteins and/or active inhibitory compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, active compound, or at least "85% substantially pure." Most specifically, the term "substantially pure" refers to a compound of at least about 95%, by dry weight, active compound, or at least "95% substantially pure." The term "substantially pure" may also be used to modify a synthetically made protein or compound of the invention, where, for example, the synthetic protein is isolated from the reagents and by-products of the synthesis reaction(s).

The term "pharmaceutical grade," as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be isolated from any carcinogen. In some instances, "pharmaceutical grade" may be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The terms "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. Thus, a variant peptide may be made by manipulation of genes encoding the polypeptide. A variant may be made by altering the basic composition or characteristics of the polypeptide, but not at least some of its fundamental activities. For example, a "variant" of azurin can be a mutated azurin that retains its ability to inhibit the growth of mammalian cancer cells. In some cases, a variant peptide is synthesized with non-natural amino acids, such as $\epsilon$-(3,5-dinitrobenzoyl)-Lys residues. Ghadiri & Fernholz, J. Am. Chem. Soc., 112:9633-9635 (1990). In some embodiments, the variant has not more than 20 amino acids replaced, deleted or inserted compared to wild-type peptide. In some embodiments, the variant has not more than 15 amino acids replaced, deleted or inserted compared to wild-type peptide. In some embodiments, the variant has not more than 10 amino acids replaced, deleted or inserted compared to wild-type peptide. In some embodiments, the variant has not more than 6 amino acids replaced, deleted or inserted compared to wild-type peptide. In some embodiments, the variant has not more than 5 amino acids replaced, deleted or inserted compared to wild-type peptide. In some embodiments, the variant has not more than 3 amino acids replaced, deleted or inserted compared to wild-type peptide.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azurin that retains its ability to inhibit angiogenesis in mammalian cells. Chemical modifications of interest include, but are not limited to, amidation, acetylation, sulfation, polyethylene glycol (PEG) modification, phosphorylation or glycosylation of the peptide. In addition, a derivative peptide maybe a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where
  X is the number of amino acid residues scored as identical matches by the sequence alignment program's or algorithm's alignment of A and B and
  Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

The present invention provides compositions comprising cupredoxin, and variants, derivatives and structural equivalents of cupredoxins, and methods to inhibit angiogenesis and/or inhibit the growth of cancer cells in mammals. The present invention specifically relates to compositions comprising cupredoxin, and their use in inhibiting the inappropriate angiogenesis that is associated with cancer and other conditions. The invention also relates to variants, derivatives and structural equivalents of cupredoxin that retain the ability to inhibit angiogenesis in mammals, and in particular the angiogenesis associated with tumor development, and compositions comprising the same. Most particularly, the invention provides compositions comprising *Pseudomonas aeruginosa* azurin, variants, derivatives and structural equivalents of azurin, and their use to treat patients with conditions related to inappropriate angiogenesis, and the angiogenesis related to tumor development, or prevent infection in those at risk thereof. Finally, the invention provides methods to study angiogenesis mammalian cells, tissues and animals by contacting the cells with cupredoxin, or variant, derivative or structural equivalent thereof, before or after inducing angiogenesis and determining variations in blood vessel development.

Previously, it was know that a redox protein elaborated by *Pseudomonas aerugisnosa*, the cupredoxin azurin, selectively enters J774 cells but not normal cells. Zaborina et al., Microbiology 146: 2521-2530 (2000). Azurin can also selectively enter human melanoma UISO-Mel-2 or human breast cancer MCF-7 cells. Yamada et al., PNAS 99:14098-14103 (2002); Punj et al., Oncogene 23:2367-2378 (2004). Azurin from *P. aeruginosa* preferentially enters J774 murine reticulum cell sarcoma cells, forms a complex with and stabilizes the tumor suppressor protein p53, enhances the intracellular concentration of p53, and induces apoptosis. Yamada et al., Infection and Immunity 70:7054-7062 (2002). Detailed studies of various domains of the azurin molecule showed that amino acids 50-77 (P28) (SEQ ID NO: 2) represented a protein transduction domain (PTD) critical for internalization and subsequent apoptotic activity. Yamada et al., Cell. Microbial. 7:1418-31, (2005).

Surprisingly, it is now known that synthesized P28 not only enters into a variety of malignant cell lines (melanoma (Mel-2), MCF-7, pancreatic, astrocytoma, glioblastoma, among others), but also non-cancerous human umbilical vein endothelial cells (HUVEC). See Example 1. P28 enters into these cells in a temperature dependent manner, but does not enter normal cells (fibroblast, normal mammary epithelium). As HUVEC cells are known to instigate angiogenesis in human embryos, the entry of P28 into HUVEC cells prompted an examination of the effect of P28 on angiogenesis. HUVEC cells (20,000 cells) were plated on Matrigel® coated wells and incubated in media containing 0-75 µM of P28. Cultures were examined under light microscopy at 4 h and 24 h post-treatment. The P28 peptide inhibited capillary tube formation of the HUVEC in a dose dependent manner, suggesting that P28 inhibits the capillary tube formation step of angiogenesis. See Example 2. Further, P28 inhibited the migration of HUVEC cells on Matrigel® in a scratch wound migration assay, indicating that P28 also inhibits the migration step of angiogenesis. See Example 3. Thus, in in vitro studies with an established angiogenesis model system, HUVEC cells on Matrigel®, P28 inhibits two critical steps in angiogenesis, capillary tube formation and cell migration.

Further, the cell morphology of HUVECs was also surprisingly changed by the addition of P28 to the growth medium. The addition of P28 to HUVECs growing on Matrigel® prevented the normal angiogenesis-related changes in cytoskeleton and other proteins that are associated with cell migration. See Example 4. In the paxillin detected cell, the paxillin was mainly localized on cell surface of the control cells, however it was more often found on F-actin fibers in the P28 treated cells (FIG. 4B). In the Fak detected cells, Fak was mainly on localized cell surface of the control cells, while it was more often found on F-actin fibers of the P28 treated cells, thus creating a less flexible and less mobile cell. The cell-cell attachment proteins CD-31/PECAM-1 were over-expressed and localized distinctly to cell-cell junctions when the HUVECs when treated with P28, thus encouraging cell-to-cell contact. Actin nucleation and branching promoting factor WASP (Wiskott Aldrich Syndrome Protein) while normally found on the cell surface in HUVECs undergoing angiogenesis, localized to the nucleus in P28 treated cells thus altering actin branching and nucleation. Finally, P28 inhibited β-catenin localization to the nucleus thus further inhibiting proliferation and cell migration in HIVECs. Therefore, several of the morphological hallmarks of angiogenesis in HUVECs are reduced or eliminated by the presence of P28, further indicating that P28 has a direct effect on cells undergoing angiogenesis.

P28 can specifically inhibit the growth the Mel-2 melanoma cells in vitro in a concentration dependant manner. See FIG. 5. Therefore, P28 is capable of not only entering cancer cells in a specific manner; it also is capable of directly inhibiting their growth. Tumor development proceeds in association with angiogenesis. P28 inhibited the growth of Mel-2 cells transplanted subcutaneously into athymic mice in a dose dependent manner. See Example 6. The incidence of measurable (>2 mm diameter) tumors 30 days post-treatment of 8 and 16 mg/kg wt i.p. was significantly lower in treatment groups, when compared to controls. Further, tumor volume was also significantly lower in animals receiving 16 mg/kg P28 as compared to control. Taken together, P28 has significant anti-tumor effects due to its selective entry into tumor cells and inhibiting their proliferation, and suppressing angiogenesis related to tumor development.

Due to the high degree of structural similarity between cupredoxins, it is likely that other cupredoxins will inhibit angiogenesis in mammals as well. Such cupredoxins may be found in, for example, bacteria or plants. It is contemplated that these other cupredoxins may be used in the compositions and methods of the invention. Further, variants, derivatives, and structural equivalents of cupredoxins that retain the ability to inhibit angiogenesis in mammalian cells may also be used in the compositions and methods of the invention. These variants and derivatives may include, but are not limited to, truncations of a cupredoxin, conservative substitutions of amino acids and proteins modifications such as PEGylation and all-hydrocarbon stabling of α-helices.

It also follows that other conditions related to inappropriate angiogenesis can be treated with cupredoxins, and azurin in particular. For example, Avastin® (bevacizumab, Genentech, South San Francisco, Calif.), a recombinant humanized monoclonal IgG1 antibody that binds to and inhibits the biologic activity of human vascular endothelial growth factor (VEGF), is not only effective in reducing angiogenesis associated with metastatic colorectal cancer, and is also highly effective in treating the inappropriate angiogenesis associated with neovascular age-related macular degeneration. Bashshur et al., Am J. Opthalmol. 142:1-9 (2006). Therefore it is likely that P28, and other cupredoxins, and variants, derivatives and structural equivalents of cupredoxins, will also inhibit inappropriate angiogenesis in conditions other than cancer, such as those associated with neovascular age-related macular degeneration. Further, it is likely that cupredoxins, and variants, derivatives and structural equivalents of cupredoxins will be effective in treating other conditions related in inappropriate angiogenesis, such as, but not limited to, diabetic retinopathy, psoriasis and rheumatoid arthritis.

Compositions of the Invention

The invention provides for peptides that are variants, derivatives or structural equivalents of cupredoxin that inhibit angiogenesis in mammalian cells, tissues and animals. The invention further provides for peptides that are variants, derivatives or structural equivalents of cupredoxin that inhibit the growth of mammalian cancer cells. The invention further provides for peptides that are variants, derivatives or structural equivalents of cupredoxin that specifically enter mammalian cancer cells. In some embodiments, the peptide is isolated. In some embodiments, the peptide is substantially pure or pharmaceutical grade. In other embodiments, the peptide is in a composition that comprises, or consists essentially of, the peptide. In another specific embodiment, the peptide does not raise an immune response in a mammal, and more specifically a human. In some embodiments, the peptide is less that a full length cupredoxin, and retains some of the functional characteristics of the cupredoxins. Specifically, in some embodiments, the peptide retains the ability to inhibit angiogenesis in HUVECs on Matrigel®.

The invention also provides compositions comprising at least one peptide that is a cupredoxin, or variant, derivative or structural equivalent of a cupredoxin, specifically in a pharmaceutical composition. In specific embodiments, the pharmaceutical composition is designed of a particular mode of administration, for example, but not limited to, oral, intraperitoneal, intravenous, or intraocular. Such compositions may be hydrated in water, or may be dried (such as by lyophilization) for later hydration. Such compositions may be in solvents other than water, such as but not limited to, alcohol.

Because of the high structural homology between the cupredoxins, it is contemplated that cupredoxins will have the same anti-angiogenesis activity as P28. In some embodiments, the cupredoxin is, but is not limited to, azurin, pseudoazurin, plastocyanin, rusticyanin, auracyanin or Laz. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis, Neisseria gonorrhea, Pseudomonas fluorescens, Pseudomonas chlororaphis, Xylella fastidiosa* or *Vibrio parahaemolyticus*. In a very specific embodiment, the azurin is from *Pseudomonas aeruginosa*. In other specific embodiments, the cupredoxin comprises an amino acid sequence that is SEQ ID NO: 1, 3-19.

The invention provides peptides that are amino acid sequence variants which have amino acids replaced, deleted, or inserted as compared to the wild-type cupredoxin. Variants of the invention may be truncations of the wild-type cupredoxin. In some embodiments, the peptide of the invention comprises a region of a cupredoxin that is less that the full length wild-type polypeptide. In some embodiments, the peptide of the invention comprises more than about 10 residues, more than about 15 residues or more than about 20 residues of a truncated cupredoxin. In some embodiments, the peptide comprises not more than about 100 residues, not more than about 50 residues, not more than about 40 residues, not more than about 30 residues or not more than about 20 residues of a truncated cupredoxin. In some embodiments, a cupredoxin has amino acid sequence identity to the peptide, and more specifically SEQ ID NOS: 1, 3-19, at least about 70% amino acid sequence identity, at least about 80% amino acid sequence identity, at least about 90% amino acid sequence identity, at least about 95% amino acid sequence identity or at least about 99% amino acid sequence identity.

In specific embodiments, the variant of cupredoxin comprises *P. aeruginosa* azurin residues 50-77, azurin residues 50-67, or azurin residues 36-88. In other embodiments, the variant of cupredoxin consists of *P. aeruginosa* azurin residues 50-77, azurin residues 50-67, or azurin residues 36-88. In other specific embodiments, the variant consists of the equivalent residues of a cupredoxin other that azurin. It is also contemplated that other cupredoxin variants can be designed that have a similar activity to azurin residues 50-77, azurin residues 50-67, or azurin residues 36-88. To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent peptide thus designed.

In one embodiment of the invention, the cupredoxin variant contains at least amino acids 57 to 89 of auracyanin B of *Chloroflexus aurantiacus* (SEQ ID NO: 20). In another embodiment of the invention, the cupredoxin variant contains at least amino acids 51-77 of *Pseudomonas syringae* azurin (SEQ ID NO: 21). In another embodiment of the invention, the cupredoxin variant contains at least amino acids 89-115 of *Neisseria meningitidis* Laz (SEQ ID NO: 22). In another embodiment of the invention, the cupredoxin variant contains at least amino acids 52-78 of *Vibrio* parahaemolyticus azurin (SEQ ID NO: 23). In another embodiment of the invention, the cupredoxin variant contains at least amino acids 51-77 of *Bordetella bronchiseptica* azurin (SEQ ID NO: 24).

The variants also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (for example Futaki et al., J. Biol. Chem. 276(8):5836-40 (2001); Papo et al., Cancer Res. 64(16):5779-86 (2004); Miller et al., Biochem. Pharmacol. 36(1):169-76, (1987); peptides containing unusual amino acids (for example Lee et al., J. Pept. Res. 63(2):69-84 (2004)), olefin-containing non-natural amino acid followed by hydrocarbon stapling (for example Schafmeister et al., J. Am. Chem. Soc. 122:5891-5892 (2000); Walenski et al., Science 305:1466-1470 (2004)), and peptides comprising ε-(3, 5-dinitrobenzoyl)-Lys residues.

In other embodiments, the peptide of the invention is a derivative of a cupredoxin. The derivatives of cupredoxin are chemical modifications of the peptide such that the peptide still retains some of its fundamental activities. For example, a "derivative" of azurin can be a chemically modified azurin that retains its ability to inhibit angiogenesis in mammalian cells, tissues or animals. Chemical modifications of interest include, but are not limited to, hydrocarbon stabling, amidation, acetylation, sulfation, polyethylene glycol (PEG) modification, phosphorylation and glycosylation of the peptide. In addition, a derivative peptide may be a fusion of a cupredoxin, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (for example Monk et al., BioDrugs 19(4): 261-78, (2005); DeFreest et al., J. Pept. Res. 63(5):409-19 (2004)), N- and C-terminal modifications (for example Labrie et al., Clin. Invest. Med. 13(5):275-8, (1990)), and olefin-containing non-natural amino acid followed by hydrocarbon stapling (for example Schafmeister et al., J. Am. Chem. Soc. 122:5891-5892 (2000); Walenski et al., Science 305:1466-1470 (2004)).

In another embodiment, the peptide is a structural equivalent of a cupredoxin. Examples of studies that determine significant structural homology between cupredoxins and other proteins include Toth et al. (Developmental Cell 1:82-92 (2001)). Specifically, significant structural homology between a cupredoxin and the structural equivalent is determined by using the VAST algorithm. Gibrat et al., Curr Opin Struct Biol 6:377-385 (1996); Madej et al., Proteins 23:356-3690 (1995). In specific embodiments, the VAST p value from a structural comparison of a cupredoxin to the structural equivalent is less than about $10^{-3}$, less than about $10^{-5}$, or less than about $10^{-7}$. In other embodiments, significant structural homology between a cupredoxin and the structural equivalent is determined by using the DALI algorithm. Holm & Sander, J. Mol. Biol. 233:123-138 (1993). In specific embodiments, the DALI Z score for a pairwise structural comparison is at least about 3.5, at least about 7.0, or at least about 10.0.

It is contemplated that the peptides of the composition of invention may be more than one of a variant, derivative and/or structural equivalent of a cupredoxin. For example, the peptides may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. Scharmeister et al., J. Am. Chem. Soc. 122:5891-5892 (2000); Walensky et al., Science 305:1466-1470 (2004). Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin may or may not bind copper.

In some embodiments, the cupredoxin, or variant, derivative or structural equivalent thereof has some of the functional characteristics of the P. aeruginosa azurin, and specifically P28. In a specific embodiment, the cupredoxins and variants, derivatives and structural equivalents of cupredoxins that may inhibit angiogenesis in mammalian cells, tissues or animals, and specifically but not limited to, HUVECs. The invention also provides for the cupredoxins and variants, derivatives and structural equivalents of cupredoxin that may have the ability to inhibit the growth of mammalian cancer cells, and specifically but not limited to, melanoma, breast, pancreas, glioblastoma, astrocytoma, or lung cancer cells. The invention also provides for the cupredoxins and variants, derivatives and structural equivalents of cupredoxin that may have the ability to enter mammalian cancer cells as compared to equivalent non-cancer cells, specifically, but not limited to, melanoma, breast, pancreas, glioblastoma, astrocytoma, or lung cancer cells. Inhibition of angiogenesis or growth of cancer cells is any decrease, or lessening of the rate of increase, of that activity that is statistically significant as compared to control treatments. The entry into cells is any the rate of entry into the cells that is statistically significant when compared to the rate of entry into equivalent normal cells.

Because it is now known that cupredoxins can inhibit angiogenesis in mammalian cells, tissues or animals, and specifically HUVECs growing on Matrigel®, it is now possible to design variants and derivatives of cupredoxins that retain this anti-angiogenesis activity. Such variants, derivatives and structural equivalents can be made by, for example, creating a "library" of various variants, derivatives and structural equivalents of cupredoxins and then testing each for anti-angiogenesis activity, and specifically anti-angiogenesis in HUVECs using one of many methods known in the art, such the exemplary method in Examples 2 and 3. It is contemplated that the resulting variants and derivatives of cupredoxins with anti-angiogenesis activity can be used in the methods of the invention, in place of or in addition to cupredoxins.

In some specific embodiments, the cupredoxin or variant, derivative or structural equivalent inhibits capillary tube formation in HUVEC cells to a degree that is statistically different from a non-treated control. A peptide can be tested for this activity by using the capillary tube formation test described in Example 3 or in Sulochana et al., J. Biol. Chem. 280:27936-27948 (2005). Other methods to determine whether capillary tube formation is inhibited another are well known in the art and may be used as well.

In some specific embodiments, the cupredoxin or variant, derivative or structural equivalent inhibits HUVEC migration in a scratch wound migration assay to a degree that is statistically different from a non-treated control. A peptide can be tested for this activity by using the capillary tube formation test described in Example 4. Other methods to determine whether HUVEC migration is inhibited are well known in the art and may be used as well.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. Cough & Clothia, Structure 12:917-925 (2004); De Rienzo et al., Protein Science 9:1439-1454 (2000). For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{4.1}$.

All of the cupredoxins possess an eight-stranded Greek key beta-barrel or beta-sandwich fold and have a highly conserved site architecture. De Rienzo et al., Protein Science 9:1439-1454 (2000). A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from *P. aeruginosa* to other proteins using VAST algorithm.

| PDB | Alignment length[1] | % aa identity | P-value[2] | Score[3] | (i) RMSD[4] | (ii) Description |
|---|---|---|---|---|---|---|
| 1AOZ A | 82 | 18.3 | 10e−7 | 12.2 | 1.9 | Ascorbate oxidase 2 |
| 1QHQ_A | 113 | 31 | 10e−7.4 | 12.1 | 1) 1.9 | 2) AuracyaninB |
| 1V54 B 1 | 79 | 20.3 | 10e−6.0 | 11.2 | 2.1 | Cytocrome c oxidase |
| 1GY2 A | 92 | 16.3 | 10e−5.0 | 11.1 | 3) 1.8 | 4) Rusticyanin |
| 3MSP A | 74 | 8.1 | 10e−6.7 | 10.9 | 2.5 | Motile Major Sperm Protein[5] |
| 1IUZ | 74 | 20.3 | 10e−5.6 | 10.3 | 5) 2.3 | 6) Plastocyanin |
| 1KGY E | 90 | 5.6 | 10e−4.6 | 10.1 | 7) 3.4 | 8) Ephrinb2 |
| 1PMY | 75 | 17.3 | 10e−4.1 | 9.8 | 9) 2.3 | 10) Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5]*C. elegans* major sperm protein proved to be an ephirin antagonist in oocyte maturation. Kuwabara, Genes and Development 17: 155-161 (2003).

Azurin

The azurins are copper containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrificans*. Murphy et al., J. Mol. Biol. 315:859-871 (2002). The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 3 shows the amino acid sequence of plastocyanin from *Phormidium laminosum*, a thermophilic cyanobacterium.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. Redinbo et al., J. Bioenerg. Biomembr. 26:49-66 (1994).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 4) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., *J. Mol. Biol.* 263: 730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 5. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. Van Dreissche et al., Protein Science 8:947-957 (1999). His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. Bond et al., J. Mol. Biol. 306: 47-67 (2001). With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. J. Biol. Chem. 267:6531-6540 (1992). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horseradish root (Koch et al., J. Am. Chem. Soc. 127:158-166 (2005)) and cucumber stellacyanin (Hart et al., *Protein Science* 5:2175-2183 (1996)) is also known. The protein has an overall fold similar to the other phytocyanins. The ephrin B2 protein ectodomain tertiary structure bears a significant similarity to stellacyanin. Toth et al., Developmental Cell 1:83-92 (2001). An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". Guss et al., J. Mol. Biol. 262:686-705 (1996). The ephrinB2 protein ectodomian tertiary structure bears a high similarity (rms deviation 1.5 Å for the 50 α carbons) to the cucumber basic protein. Toth et al., Developmental Cell 1:83-92 (2001).

The Cu atom has the normal blue copper NNSS' co-ordination with bond lengths Cu—N(His39)=1.93 Å, Cu—S (Cys79)=2.16 Å, Cu—N(His84)=1.95 A, Cu—S(Met89) =2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Methods of Use

The invention provides methods to treat a mammalian patient suffering from cancer, recovering from cancer, recovered from cancer or at risk to get cancer comprising administering to the patient at least one polypeptide that is a cupredoxin, or variant, derivative or structural equivalent thereof, as described above. Specifically, cancers that may be treated with the compositions of the invention include, but are not limited to, melanoma, breast, pancreas, glioblastoma, astrocytoma, or lung cancer. The invention further provides methods to treat patients suffering from, recovering from, recovered from or at risk of getting other conditions related to inappropriate angiogenesis comprising administering to the patient at least one polypeptide that is a cupredoxin, or variant, derivative or structural equivalent thereof. These conditions include, but are not limited to, neovascular age-related macular degeneration, diabetic retinopathy, psoriasis and rheumatoid arthritis. In specific embodiments, the patient is human.

The invention further includes methods to study angiogenesis comprising contacting mammalian cells with a composition comprising cupredoxin, or variant, derivative or structural equivalent thereof. In some embodiments, the cells are HUVECs, while in others they are other cells that undergo angiogenesis. The methods of the invention further include methods to study conditions related to inappropriate angiogenesis comprising contacting mammalian cells with a composition comprising cupredoxin, or variant, derivative or structural equivalent thereof. In these methods, cells may be those which undergo angiogenesis in mammalian patients suffering from the condition.

The compositions comprising a cupredoxin or variant, derivative or structural equivalent thereof can be administered to the patient by many routes and in many regimens that will be well known to those in the art. In specific embodiments, the cupredoxin, or variant, derivative or structural equivalent thereof is administered intravenously, intramuscularly, subcutaneously or intraoccularly. The compositions may be administered to the patient by any means that delivers the peptides to the site of inappropriate angiogenesis.

In one embodiment, the methods may comprise co-administering to a patient one unit dose of a composition comprising a cupredoxin or a variant, derivative or structural equivalent of cupredoxin and one unit dose of a composition comprising another anti-cancer drug, in either order, administered at about the same time, or within about a given time following the administration of the other, for example, about one minute to about 60 minutes following the administration of the other drug, or about 1 hour to about 12 hours following the administration of the other drug. Such drugs include, for example, those listed herein and specifically 5-fluorouracil; Interferon α; Methotrexate; Tamoxifen; and Vincristine. The above examples are provided for illustration only, many other such compounds are known to those skilled in the art. The compounds of the invention may also be used in conjunction with radiation therapy and surgery.

Other drugs suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17.beta.-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, caminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful to co-administer with the compositions of the invention include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which can be employed together with any NHR modulators (including, but not limited to, those of present invention) such as AR modulators, ER modulators, with LHRH modulators, or with surgical techniques.

In another embodiment, the cupredoxin, variant, derivative or structural equivalent thereof may be co-administered with a drug for the treatment of neovascular age-related macular degeneration. Such drugs include, but are not limited to, Lucentis® (Genetech, South San Francisco Calif., Ranibizumab, vitreous injection), Macugen® (OSI Pharmaceuticals, Melville N.Y., pegaptanib, vitreous injection), Retaane® (Alcon, Fort Worth Tex., Anecortave, posterior juxtascleral injection), AdPEDF (GenVec, Gaithersburg Md., anti-angiogenic gene therapy, intravitreal or sub-Tenon injection), EVIZON® (Genaera, Plymouth Meeting, Pa., anti-angiogenic aminosterol, Squalamine, intravenous injection), Combretastatin AAdPEDF4 Prodrug (OXiGENE, Waltham Mass., CA4P, Vascular Targeting agentc), Cand5 (Acuity Pharmaceuticals, Inc., Philadelphia Pa., siRNA targeting Vascular Endothelial Growth Factor (VEGF), Sirna-027® (Sirna Therapeutics, San Francisco, Calif., siRNA targeting Vascular Endothelial Growth Factor Receptor-1 (VEGFR-1)), Celecoxib with PDT (Celebrex®, Oral anti-inflammatory drug), and Envision® TD (Control Delivery Systems, Watertown, Mass., fluocinolone implant sustained release steroid implant in vitreous).

In another embodiment, the cupredoxin, variant, derivative or structural equivalent thereof may be co-administered with a drug for the treatment of diabetic retinopathy. Surgical treatment is also contemplated as a co-treatment with the compositions of the invention.

In another embodiment, the cupredoxin, variant, derivative or structural equivalent thereof may be co-administered with a drug for the treatment of psoriasis. Such drugs include, but are not limited to, Amevive®, Raptiva®, Enbrel®, Humira®, Remicade®, Cyclosporine, Neoral®, Methotrexate, Soriatane®, Accutane®, Hydrea®, mycophenolate mofetil, sulfasalazine, and 6-Thioguanine.

In another embodiment, the cupredoxin, variant, derivative or structural equivalent thereof may be co-administered with a drug for the treatment of rheumatoid arthritis Such drugs include, but are not limited to, Methotrexate (Rheumatrex®, Folex PFS®), Sulfasalazine (Azulfidine®), Leflunomide (Arava®), Gold salts (aurothiomalate, auranofin [Ridaura®]), D-penicillamine, Hydroxychloroquine (Plaquenil®), Azathioprine (Imuran®), Cyclosporine (Neoral®), Etanercept (Enbrel®), Infliximab (Remicade®), Adalimumab (Humira®), Anakinra (Kineret®), Abatacept (Orencia®), Prednisone (Deltasone®, Meticorten®, Orasone®), Betamethasone (Celestone®), Nonsteroidal anti-inflammatory drugs (NSAIDs), and COX-2 inhibitors (celecoxib, Celebrex®).

Pharmaceutical Compositions Comprising Cupredoxin, or Variant, Derivative or Structural Equivalent Thereof Pharmaceutical compositions comprising cupredoxin or variant, derivative or structural equivalents thereof, can be manufactured in any conventional manner, e.g., by conventional mixing, dissolving, granulating, dragee-making, emulsifying, encapsulating, entrapping, or lyophilizing processes. The substantially pure or pharmaceutical grade cupredoxin or variants, derivatives and structural equivalents thereof can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., Id. In some embodiments, the composition comprising a cupredoxin or variant, derivative or structural equivalent thereof can be formulated and used directly as injectibles, for subcutaneous and intravenous injection, among others. The injectable formulation, in particular, can advantageously be used to treat patients that are at risk of, likely to have or have a condition related to inappropriate angiogenesis. The composition comprising a cupredoxin or variant, derivative or structural equivalent thereof can also be taken orally after mixing with protective agents such as polypropylene glycols or similar coating agents.

When administration is by injection, the cupredoxin or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [$Na^+$] | [$Cl^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L $K^+$ and 3 mmol/L $Ca^{2+}$.

When administration is by inhalation, the cupredoxin or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or variant, derivative or structural equivalent thereof may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin or variants and derivatives thereof compositions may also be formulated in compositions containing conventional suppository bases.

When administration is oral, a cupredoxin or variant, derivative or structural equivalent thereof can be readily formulated by combining the cupredoxin or variant, derivative or structural equivalent thereof with pharmaceutically acceptable carriers well known in the art. A solid carrier, such as mannitol, lactose, magnesium stearate, and the like may be employed; such carriers enable the cupredoxin and variants, derivatives or structural equivalent thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or variant, derivative or structural equivalent thereof allow for the release of cupredoxin or variant, derivative or structural equivalent thereof over extended periods of time, such that without the sustained release formulation, the cupredoxin or variant, derivative or structural equivalent thereof would be cleared from a subject's system, and/or degraded by, for example, proteases and simple hydrolysis before eliciting or enhancing a therapeutic effect.

The half-life in the bloodstream of the peptides of the invention can be extended or optimized by several methods well known to those in the art. The peptide variants of the invention may include, but are not limited to, various variants that may increase their stability, specific activity, longevity in the bloodstream, and/or decrease immunogenicity of the cupredoxin, while retaining the ability of the peptide to inhibit angiogenesis, to enter mammal cancer cells and/or inhibit the growth of mammalian cancer cells. Such variants include, but are not limited to, those which decrease the hydrolysis of the peptide, decrease the deamidation of the peptide, decrease the oxidation, decrease the immunogenicity, increase the structural stability of the peptide or increase the size of the peptide. Such peptides also include circularized peptides (see Monk et al., BioDrugs 19(4):261-78, (2005); DeFreest et al., J. Pept. Res. 63(5):409-19 (2004)), D,L-peptides (diastereomer), Futaki et al., J. Biol. Chem. February 23; 276(8):5836-40 (2001); Papo et al., Cancer Res. 64(16): 5779-86 (2004); Miller et al., Biochem. Pharmacol. 36(1): 169-76, (1987)); peptides containing unusual amino acids (see Lee et al., J. Pept. Res. 63(2):69-84 (2004)), N- and C-terminal modifications (see Labrie et al., Clin. Invest. Med. 13(5):275-8, (1990)), hydrocarbon stapling (see Schafmeister et al., J. Am. Chem. Soc. 122:5891-5892 (2000); Walenski et al., Science 305:1466-1470 (2004)) and PEGylation. Of particular interest are d-isomerization (substitution) and modification of peptide stability via D-substitution or L-amino acid substitution.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin or Variant, Derivative or Structural Equivalent Thereof The cupredoxin or variant, derivative or structural equivalent thereof can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) or vitreous administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or variant, derivative or structural equivalent thereof are useful for the treatment and/or prophylaxis of conditions related in inappropriate angiogenesis, alone or in combination with other active agents. The appropriate dosage will, of course, vary depending upon, for example, the compound of cupredoxin or variant, derivative or structural equivalent thereof employed, the host, the mode of administration and the nature and severity of the conditions being treated. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or over. Alternatively, dosing can be continuous using patches, i.v. administration and the like.

The exact formulation, route of administration, and dosage is determined by the attending physician in view of the patient's condition. Dosage amount and interval can be adjusted individually to provide plasma levels of the active cupredoxin or variant, derivative or structural equivalent thereof which are sufficient to maintain therapeutic effect. Generally, the desired cupredoxin or variant, derivative or structural equivalent thereof is administered in an admixture with a pharmaceutical carrier selected with regard to the intended route of administration and standard pharmaceutical practice.

In one aspect, the cupredoxin or variant, derivative or structural equivalent thereof is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and variants and derivatives thereof polynucleotide to an inducible promoter can control the expression of the cupredoxin and variants and derivatives thereof in response to specific factors. Examples of classic inducible promoters include those that are responsive to α-interferon, heat shock, heavy metal ions, and steroids such as glucocorticoids (Kaufman, Methods Enzymol. 185:487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin, or Variant, Derivative or Structural Equivalent Thereof In one aspect, the invention provides regimens or kits comprising one or more of the following in a package or container: (1) a biologically active composition comprising at least one cupredoxin or variant, derivative or structural equivalent thereof; (2) an anti-viral or anti-bacterial drug, specifically an anti-cancer drug, an anti-macular degeneration drug, an anti psoriasis drug or an anti-rheumatoid arthritis drug.

When a kit is supplied, the different components of the composition may be packaged in separate containers, if appropriate, and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized cupredoxin and variants, derivatives and structural equivalents thereof, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin and Variants, Derivatives and Structural Equivalents Thereof Cupredoxin or variant, derivative or structural equivalents thereof may be chemically modified or genetically altered to produce variants and derivatives as explained above. Such variants and derivatives may be synthesized by standard techniques.

In addition to naturally-occurring allelic variants of cupredoxin, changes can be introduced by mutation into cupredoxin coding sequence that incur alterations in the amino acid sequences of the encoded cupredoxin that do not significantly alter the ability of cupredoxin to inhibit angiogenesis. A "non-essential" amino acid residue is a residue that can be altered from the wild-type sequences of the cupredoxin without altering biological activity, whereas an "essential" amino acid residue is required for such biological activity. For example, amino acid residues that are conserved among the cupredoxins are predicted to be particularly non-amenable to alteration, and thus "essential."

Amino acids for which conservative substitutions that do not change the activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the biological activity of the compound.

TABLE 3

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the cytotoxic factor function. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154.329-350 (1987)), cassette mutagenesis, restriction selection mutagenesis (Wells et al., Gene 34:315-323 (1985)) or other known techniques can be performed on the cloned DNA to produce the cupredoxin variant DNA.

Known mutations of cupredoxins can also be used to create variant cupredoxin to be used in the methods of the invention. For example, the C112D and M44KM64E mutants of azurin are known to have cytotoxic and growth arresting activity that is different from the native azurin, and such altered activity can be useful in the treatment methods of the present invention. One embodiment of the methods of the invention utilizes cupredoxin and variants and derivatives thereof retaining the ability inhibit angiogenesis. In another embodiment, the methods of the present invention utilize cupredoxin variants such as the M44KM64E mutant, having the ability to cause cellular growth arrest.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof and, therefore, only such limitations should be imposed as are indicated by the appended embodiments.

EXAMPLES

Example 1

Entry of P28 into Human Umbilical Vein Endothelial Cells

P28 was labeled with 20 µM Alexafluor® 568 (Molecular Probes, Eugene, Oreg.). Indicated cell lines were cultured on cell culture coated cover slips overnight at 37° C. Pre-warmed media containing labeled peptide was added at indicated concentrations. After incubation with the labeled peptide, the cover slips were washed 3× with PBS and fixed in formalin for 5 minutes. Cover slips were then mounted in media containing 1.5 µg ml$^{-1}$ DAPI for nuclear staining (VECTASHIELD®, Vector Laboratories, Burlingame, Calif.). Analysis was performed with a confocal microscope (Model LC510, Carl Zeiss, Thornwood, N.Y.).

P28 effectively entered malignant cell lines originating from melanoma, breast, pancreas, glioblastoma, astrocytoma, and lung (FIG. 1A). P28 was also efficiently entered HUVEC cells (FIG. 1C). No significant entry was observed in other "normal" cell lines originating from skin fibroblasts, breast and pancreas FIG. 1B). Therefore, in addition to specifically entering mammalian cancer cells, P28 also specifically enters HUVEC cells.

This experiment shows that the P. aeruginosa azurin 50-77 peptide has activity that inhibits capillary tube formation in endothelial cells, one step in angiogenesis. The P. aeruginosa azurin 50-77 peptide can therefore be used to control angiogenesis and hence be utilized as a cancer treatment, and treatment of other conditions related to inappropriate angiogenesis.

Example 2

Effects of P28 on HUVEC Capillary Tube Formation on Matrigel®

Matrigel® Matrix (Becton Dickinson Biosciences, San Jose Calif.) is a solubulized basement membrane preparation extracted from EHS mouse sarcoma, a tumor rich in ECM proteins. Its major component is laminin, followed by collagen IV, heparan sulfate proteoglycans, and entactin 1. At room temperature, Matrigel® Matrix polymerizes to produce biologically active matrix material resembling the mammalian cellular basement membrane. Cells behave as they do in vivo when they are cultured on Matrigel® Matrix. It provides a physiologically relevant environment for studies of cell morphology, biochemical function, migration or invasion, and gene expression. Matrigel® Matrix serves as a substrate for in vitro endothelial cell invasion and tube formation assays.

The effects of P28 on the capillary tube formation of HUVEC cells were investigated using Matrigel®. HUVEC cells were plated (15,000 cells/well) on Matrigel® coated 8 well chamber slides with 20 ng/ml VEGF and in the presence or absence of peptide. P28 concentrations of 0 µM (control), 0.10 µM, 0.30 µM, 0.92 µM, 2.77 µM, 8.33 µM, 25 µM and 75 µM were used. Cells were stained 4 h and 24 h post-treatment with calcein AM, and capillary tube formation was examined using a fluorescence microscope (FIG. 2A). The results show that as little as 0.10 µM prevented capillary tube formation by HUVEC cells by about 50% (FIG. 2A). P28 therefore inhibits tube formation of HUVEC cells, and will therefore also inhibit the capillary tube formation related to angiogenesis.

Example 3

Effects of P28 on HUVEC Motility

The effects of P28 on HUVEC motility was investigated with the scratch wound migration assay. HUVEC cells were plated in 60 mm tissue culture dishes and allowed to reach 90% confluence. After removing the media, cell layers were wounded using a 1 ml sterile plastic pipette tip. Plates were rinsed with culture media. Media with 20 ng/ml VEGF alone or media with 20 ng/ml VEGF and containing P28 peptide was then added to the plates. One dish was scratched as above and fixed immediately in order to mark exact wound area. FIG. 3A. After 24 h, cultures were fixed and stained for F-actin and nuclei using Phalloidin and Hoechst stain. Scratched areas were examined using a florescence microscope and photographed. The number of cells that migrated into the scratched area was counted in the control (FIG. 3B) and peptide treated dishes (FIG. 3C).

The number of HUVECs that migrated into the scratch wound in the cells treated with P28 was about half that of those that migrated into the scratch wound in the control. Figure D. Therefore, the presence of P28 inhibited the motility of HUVECs undergoing angiogenesis.

Example 4

Effects of P28 on HUVEC Structural Proteins

The effects of P28 on HUVEC structural proteins was studied to gain a better understanding of the way P28 affects these cells. HUVEC cells plated on Matrigel® coated cover slips were incubated with 20 ng/ml VEGF in the presence or absence of 25 µM P28 peptide for 4 h or 24 h. After incubation, cells were rinsed in PBS, fixed in buffered formalin and permeablized in 0.2% triton in PBS. Cells were incubated with indicated antibodies for 90 min, and if necessary incubated with a specific secondary antibody, and then mounted in DAPI containing mounting media. Analysis was performed with a confocal microscope (model LC510, Carl Zeiss). Proteins examined are as follows: CD-31 protein present at intercellular junctions that is necessary for cell to cell attachment), Fak (focal adhesion kinase), Paxillin, Vinculin (critical adhesion assembly proteins), WASP (Wiskott Aldrich Syndrome protein, required for nucleation and elongation of F-actin fibers), β-catenin (required for cell survival, regulation of cell surface proteins).

Figure 4A:
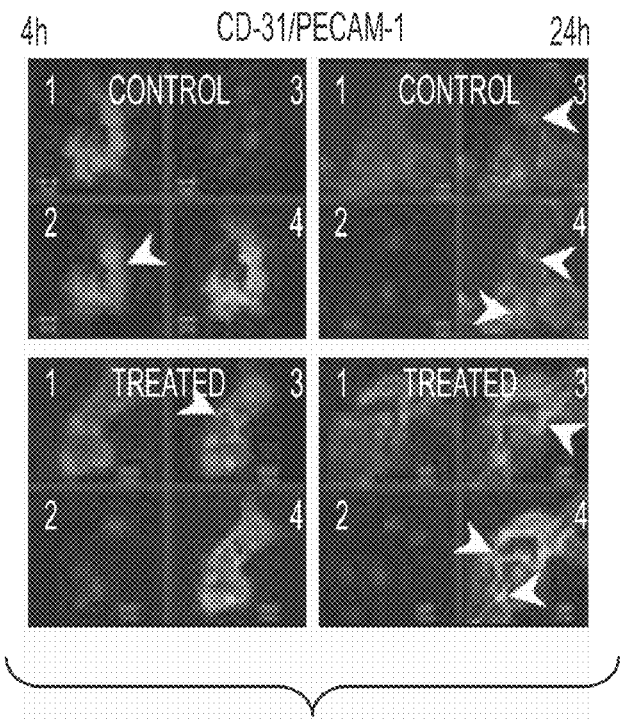
FIG. 4A is CD31/PECAM-1.
Figure 4B:
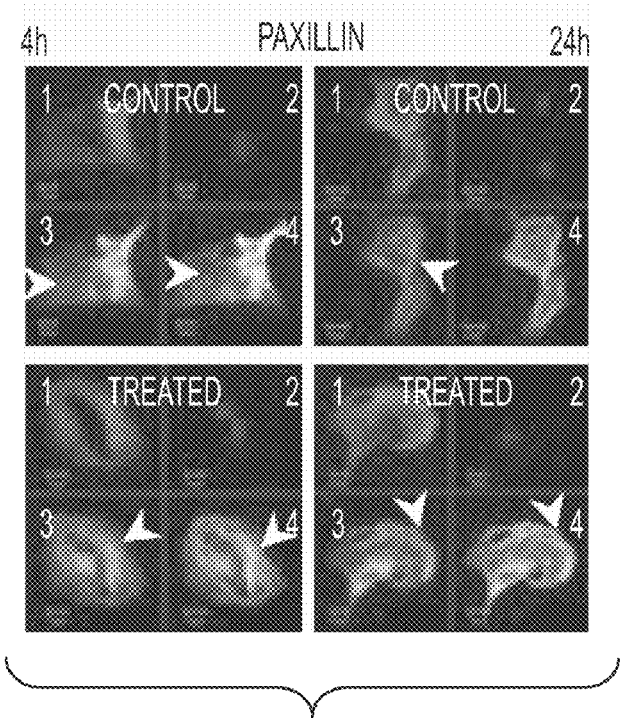
FIG. 4B is paxillin.
Figure 4C:
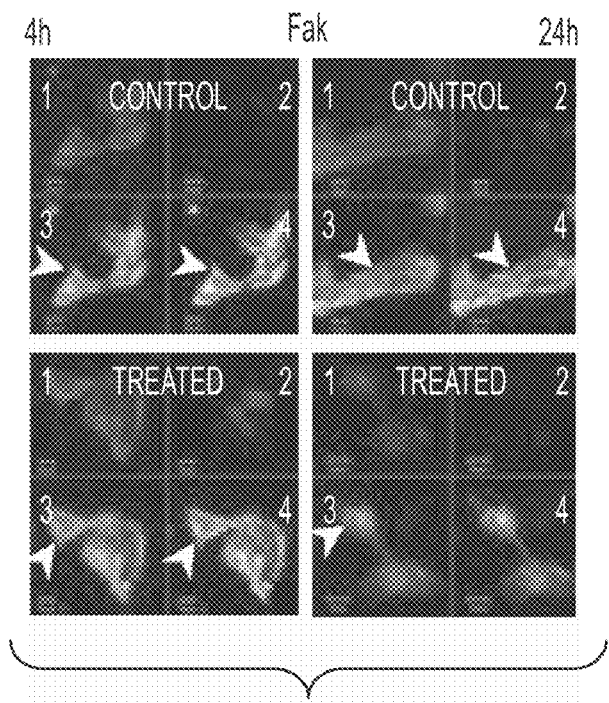
FIG. 4C is Fak.
Figure 4D:
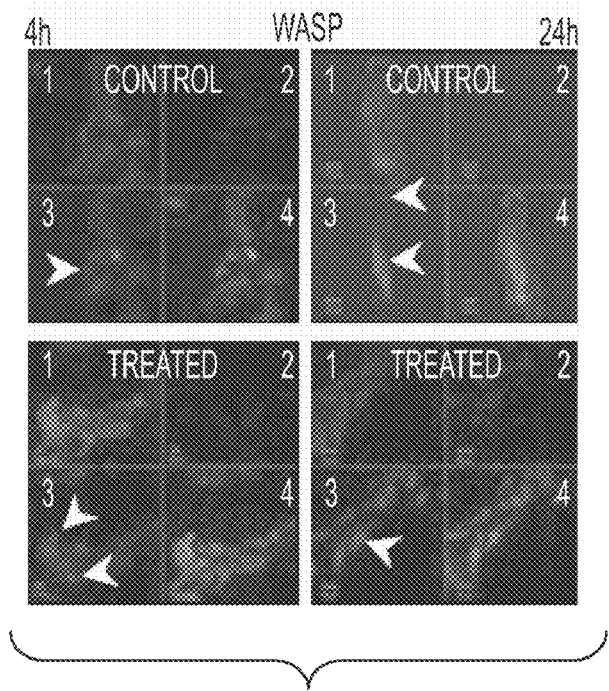
FIG. 4D is WASP.
Figure 4E:
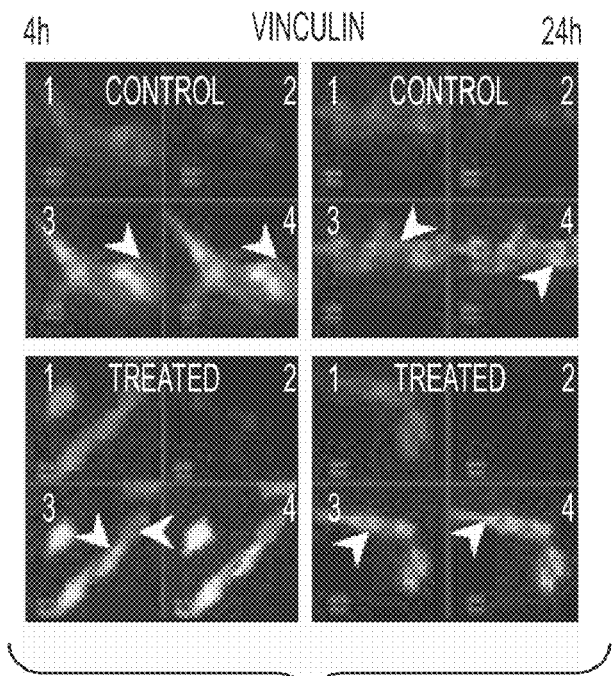
FIG. 4E is vinculin.
Figure 4F:
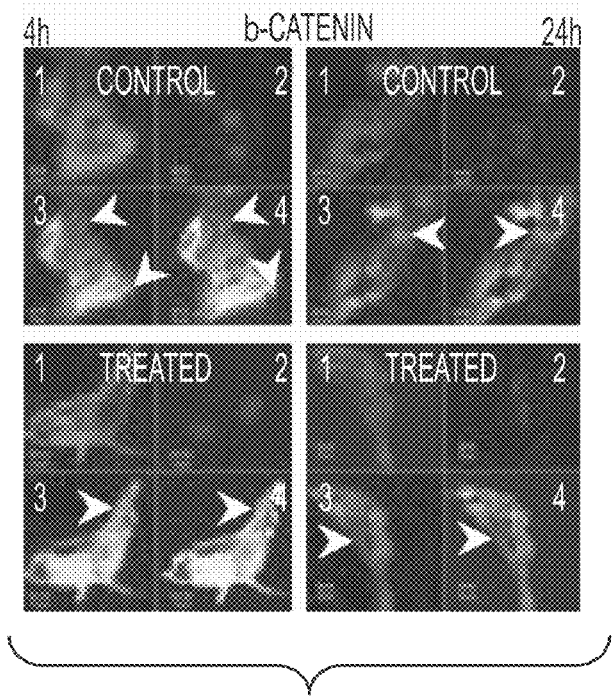
FIG. 4F is β-catenin. Each figure is divided into four panes which show the image of the localization of the fluorescent markers used. Each pane is numbered to indicate the fluorescent marker detected: 1=F-actin; 2=DAPI; 3=FITC-Protein of interest; 4=merged image. Arrows indicate the localization of the protein of interest.

In the CD31/PECAM1 detected cells, pronounced CD31/PECAM localization was found at cell/cell junctions in P28 treated cells as compared to control (FIG. 4A). In the paxillin detected cell, the paxillin was mainly localized on cell surface of the control cells, however it was more often found on F-actin fibers in the P28 treated cells (FIG. 4B). In the Fak detected cells, Fak was mainly on localized cell surface of the control cells, while it was more often found on F-actin fibers of the P28 treated cells (FIG. 4C). In the WASP detected cells, at 4 h WASP localization was mostly nuclear in control cells, while WASP was localized on the nucleus and at the cell surface in P28 treated cells (FIG. 4 D). At 24 h, WASP was mostly localized at the cell surface in control cells, while it was mostly localized in the nucleus in P28 treated cells (FIG. 4D). In the vinculin detected cells, vinculin was localized mainly on the cell surface in control cells, while vinculin was more often localized on F-actin fibers in P28 treated cells (FIG. 4E). In β-catenin detected cells, at 4 h, β-catenin localization was mostly cytoplasmic with some on the cell surface in the control cells, while β-catenin was mostly localized on the cell membrane with some in the perinuclear space in the P28 treated cells. At 24 h, β-catenin localization was mostly on the cell membrane and in the nucleus in the control cells, while β-catenin was localized on the cell membrane and perinuclear area in P28 treated cells. Therefore, the presence of P28 prevented the structural changes normally found in HUVECs undergoing angiogenesis.

Example 5

In Vitro Growth Inhibition of Human Melanoma Cells by P28

The ability of P28 to inhibit the growth of human melanoma Mel-2 cells in vitro was determined. Mel-2 cells were plated in 24 well culture plates at 10,000-12,000 cells/well and allowed to attach to the plate overnight. Cells were then incubated at 37° C. in media alone (MEM-E with 10% FBS) or media containing P28 peptide. P28 was added at 5 µM, 50 µM, and 100 µM. The number of cells in each well was counted at 0h, 24 h, 48 h and 72 h. The number of cells in each well was counted using a Coulter counter at the indicated time.

Figure 5:
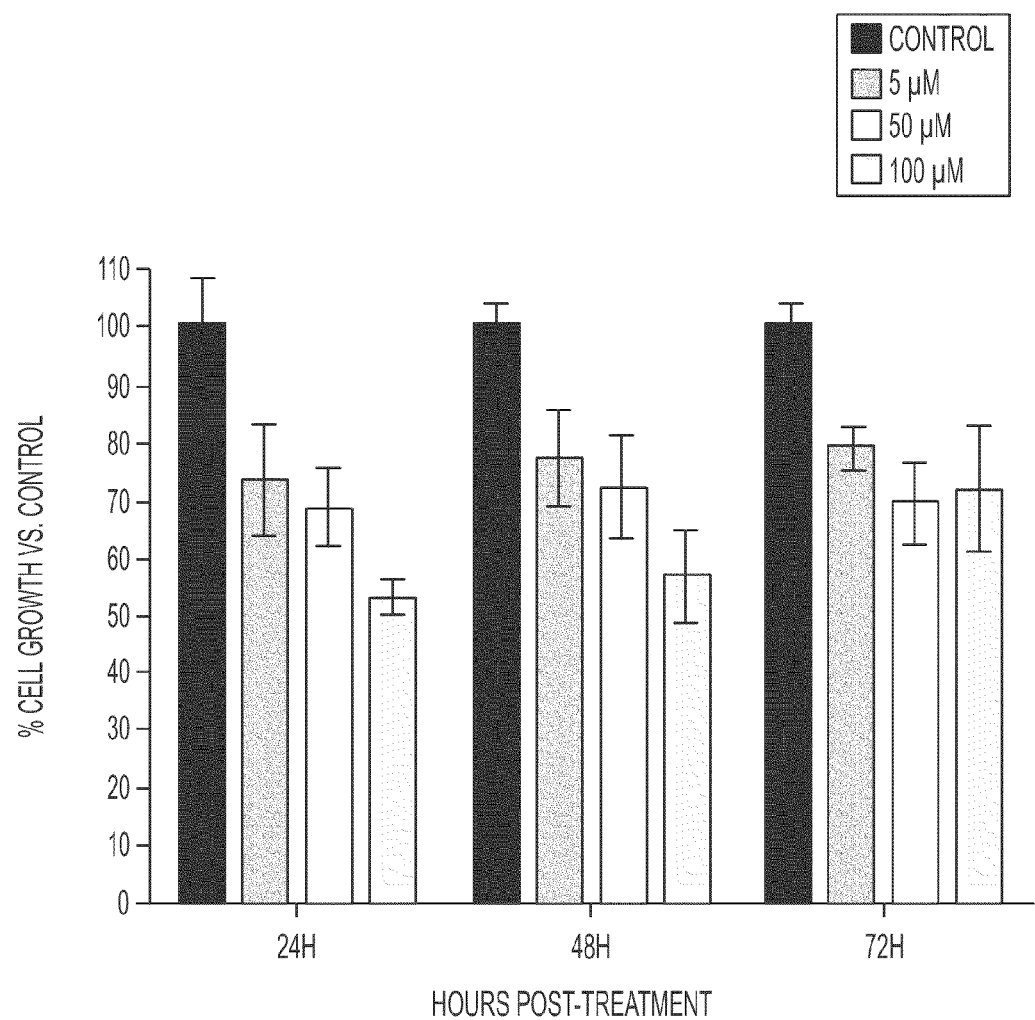
FIG. 5.

The results show that P28 inhibits growth of Mel-2 cells in a concentration dependent manner. P28 inhibited the Mel-2 cell growth by about 50% at 100 µM and 24 h (FIG. 5). These results indicate that P28 inhibits the growth of cancer cells, specifically human melanoma-2 cells.

Example 6

In Vivo Anti-Tumor Activity of P28 Peptides

One million mel-2 cells were injected subcutaneously into the dorsal flank of 3-4 week old athymic mice (n=13 per group). Animals received daily i.p. injections of PBS only, 8 mg, or 16 mg per kg body weight (b.w.) of P28 peptide in PBS. Animals were examined daily for the development of palpable tumors. Once the tumor developed, tumor size was measured using a caliper and tumor volume was determined.

Figure 6A:
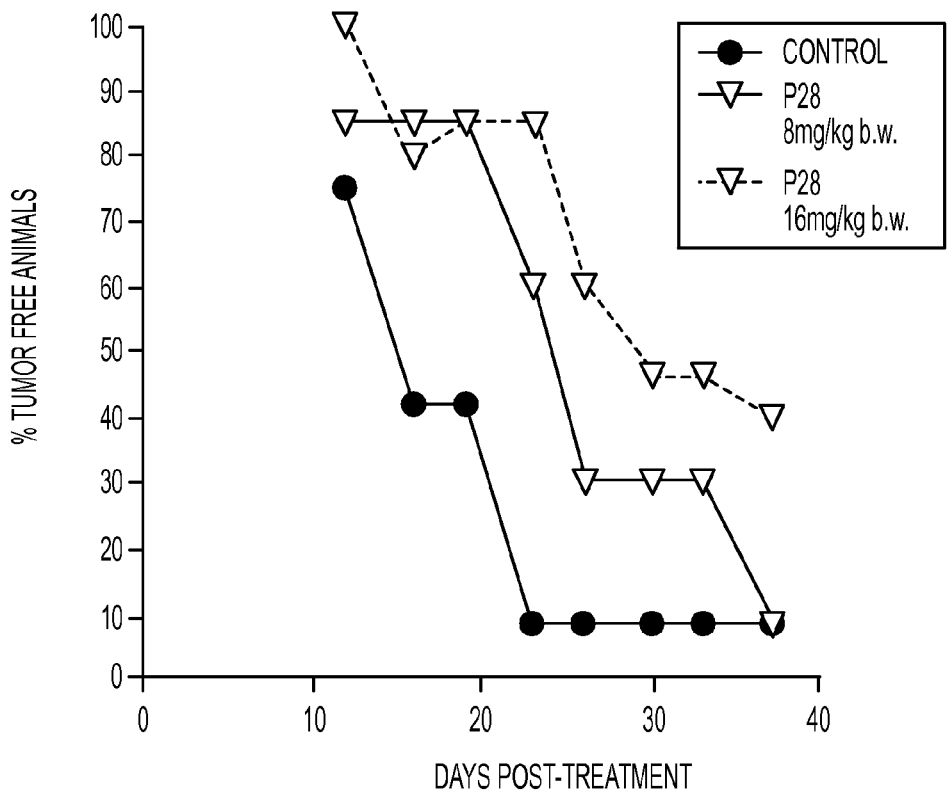
FIG. 6A shows the incidence of tumor occurrence after initiation of treatment with a graph indicating % of tumor free animals at days post treatment with Mel-2 cells.
Figure 6B:
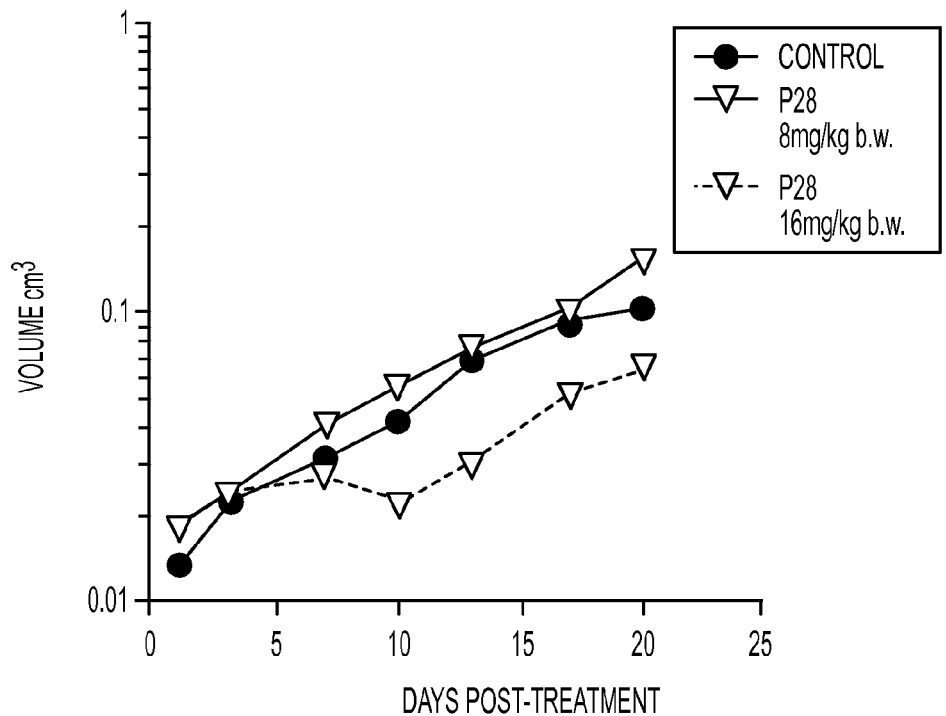
FIG. 6B shows the tumor size after initiation of treatment with a graph indicating the average volume of the tumors ($cm^3$) at days post treatment with Mel-2 cells.

P28 inhibited the tumor incidence and growth in the mice. With the treatment of 16 mg/kg b.w., about 50% of the animal were tumor-free 40 days after the mel-2 cells were injected, while only about 95% of the control animals had tumors 22 days after the mel-2 cells were injected (FIG. 6A). P28 also inhibited the growth of the tumors by about 30% at 20 days post treatment with 16 mg/kg b.w. P28 (FIG. 6B). These results indicate that P28 can prevent the slow and prevent the develop of tumors, as well as slow the growth of existing tumors in vivo, and thus would make an effective therapeutic for cancer prevention and treatment in humans.

What is claimed is:

1. An isolated peptide consisting of SEQ ID NO:2 or a truncation of SEQ ID NO:2, wherein the truncation comprises amino acid residues 1-18 of SEQ ID NO:2, and wherein the isolated peptide is capable of inhibiting capillary tube formation by HUVEC cells in vitro.

2. The isolated peptide of claim 1 consisting of amino acid residues 1-18 of SEQ ID NO:2.

3. A pharmaceutical composition comprising the isolated peptide of claim 1 and a pharmaceutically acceptable carrier.

4. The pharmaceutical composition of claim 3 wherein the pharmaceutically acceptable carrier is suitable for intravenous administration.

5. A kit comprising the composition of claim 4 in a vial.

* * * * *

UNITED STATES PATENT AND TRADEMARK OFFICE
CERTIFICATE OF CORRECTION

PATENT NO. : 7,556,810 B2
APPLICATION NO. : 11/488693
DATED : July 7, 2009
INVENTOR(S) : Rajeshwari R. Mehta et al.

Page 1 of 1

It is certified that error appears in the above-identified patent and that said Letters Patent is hereby corrected as shown below:

Column 1, lines 26-32:

"STATEMENT OF GOVERNMENTAL INTEREST
The subject matter of this application has been supported by research grants from the National Institutes of Health (NIH), Bethesda, Maryland, U.S.A., (Grant Numbers AI 16790-21, ES 04050-16, AI 45541, CA09432 and N01-CM97567). The government may have certain rights in this invention." should be deleted.

Signed and Sealed this

Third Day of August, 2010

David J. Kappos
*Director of the United States Patent and Trademark Office*